US010092578B2

(12) United States Patent
Kanamathareddy et al.

(10) Patent No.: US 10,092,578 B2
(45) Date of Patent: *Oct. 9, 2018

(54) ACTIVE AGENTS AND THEIR OLIGOMERS AND POLYMERS

(71) Applicant: Polymerix Corporation, Chapel Hill, NC (US)

(72) Inventors: Suseela Kanamathareddy, Chapel Hill, NC (US); Karen J. Giroux, Chapel Hill, NC (US)

(73) Assignee: Polymerix Corporation, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,282

(22) Filed: Jul. 9, 2015

(65) Prior Publication Data

US 2016/0058776 A1 Mar. 3, 2016

Related U.S. Application Data

(63) Continuation of application No. 13/467,623, filed on May 9, 2012, now Pat. No. 9,108,070, which is a continuation of application No. 12/813,776, filed on Jun. 11, 2010, which is a continuation of application No. 12/441,347, filed as application No. PCT/US2007/078426 on Sep. 13, 2007.

(60) Provisional application No. 60/825,465, filed on Sep. 13, 2006.

(51) Int. Cl.
| | |
|---|---|
| *C07C 69/76* | (2006.01) |
| *A61K 31/616* | (2006.01) |
| *A61K 8/37* | (2006.01) |
| *A61K 8/69* | (2006.01) |
| *A61K 8/81* | (2006.01) |
| *A61Q 17/00* | (2006.01) |
| *A01N 39/02* | (2006.01) |
| *A61K 47/54* | (2017.01) |

(52) U.S. Cl.
CPC ............ *A61K 31/616* (2013.01); *A01N 39/02* (2013.01); *A61K 8/37* (2013.01); *A61K 8/69* (2013.01); *A61K 8/8164* (2013.01); *A61K 47/542* (2017.08); *A61Q 17/005* (2013.01)

(58) Field of Classification Search
None
See application file for complete search history.

(56) References Cited

U.S. PATENT DOCUMENTS

| | | | |
|---|---|---|---|
| 2,607,799 A | 8/1952 | Weesner | |
| 4,062,855 A | 12/1977 | Allan et al. | |
| 4,126,445 A | 11/1978 | Allan et al. | |
| 4,164,560 A | 8/1979 | Folkman et al. | |
| 4,192,308 A | 3/1980 | Michaels | |
| 4,298,595 A | 11/1981 | Parkinson et al. | |
| 4,502,976 A | 3/1985 | Heller | |
| 4,591,496 A | 5/1986 | Cohen et al. | |
| 4,684,620 A | 8/1987 | Hruby et al. | |
| 4,757,128 A | 7/1988 | Domb et al. | |
| 4,792,598 A | 12/1988 | Ziegast | |
| 4,857,311 A | 8/1989 | Domb et al. | |
| 4,868,274 A | 9/1989 | Gupta et al. | |
| 4,886,870 A | 12/1989 | D'Amore et al. | |
| 4,888,176 A | 12/1989 | Langer et al. | |
| 4,891,225 A | 1/1990 | Langer et al. | |
| 4,906,474 A | 3/1990 | Langer et al. | |
| 4,916,204 A | 4/1990 | Domb et al. | |
| 4,938,949 A | 7/1990 | Borch et al. | |
| 4,997,904 A | 3/1991 | Domb | |
| 4,999,417 A | 3/1991 | Domb | |
| 5,032,216 A | 7/1991 | Felten | |
| 5,082,925 A | 1/1992 | Shalaby et al. | |
| 5,160,745 A | 11/1992 | DeLuca et al. | |
| 5,175,235 A | 12/1992 | Domb et al. | |
| 5,220,051 A | 6/1993 | Sotoya et al. | |
| 5,259,968 A | 11/1993 | Emert et al. | |
| 5,264,540 A | 11/1993 | Cooper et al. | |
| 5,290,494 A | 3/1994 | Coombes et al. | |
| 5,317,079 A | 5/1994 | Domb et al. | |
| 5,364,725 A | 11/1994 | Wilson et al. | |
| 5,498,729 A | 3/1996 | Domb | |
| 5,512,131 A | 4/1996 | Kumar et al. | |
| 5,514,764 A | 5/1996 | Frechet et al. | |

(Continued)

FOREIGN PATENT DOCUMENTS

| | | |
|---|---|---|
| AU | 750424 | 3/2003 |
| CA | 2393676 | 7/2002 |

(Continued)

OTHER PUBLICATIONS

Wagner, Phenolic Compounds in Plants of Pharmaceutical Interest (Biochemistry of Plant Phenolics, Recent Advances in Phytochemistry vol. 12, Plenum Press, New York, 1979).*
Pinther et al. (Makromolekulare Chemie, Rapid Communications, 1990, 11(8), 403).*
Aebischer, P., et al., "Basic fibroblast growth factor released from synthetic guidance channels facilitates peripheral nerve regeneration across long nerve gaps", *Journal of Neuroscience Research*, 23(3), 282-289, (Jul. 1989).
Anastasiou, T.J., "Novel, Degradable Polyanhydrides", *25th Annual Meeting Transactions of the Society for Biomaterials*, Abstract, 79, (1999).

(Continued)

*Primary Examiner* — Clinton A Brooks
*Assistant Examiner* — Jennifer C Sawyer
(74) *Attorney, Agent, or Firm* — Haukaas Fortius PLLC; Michael H. Haukaas

(57) ABSTRACT

Conjugates comprising at least two active agents linked by a diglycolic acid or polyglycol diacid linker are disclosed. The invention also concerns oligomers and polymers of these conjugates and their use in therapeutic and industrial applications for localized, immediate or fast release delivery of an active agent, such as an anti-microbial, anti-infective, or antiseptic agent.

16 Claims, 6 Drawing Sheets

(56) References Cited

U.S. PATENT DOCUMENTS

| | | |
|---|---|---|
| 5,518,730 A | 5/1996 | Fuisz |
| 5,545,409 A | 8/1996 | Laurencin et al. |
| 5,629,009 A | 5/1997 | Laurencin et al. |
| 5,660,851 A | 8/1997 | Domb |
| 5,721,131 A | 2/1998 | Rudolph et al. |
| 5,776,748 A | 7/1998 | Singhvi et al. |
| 5,798,115 A | 8/1998 | Santerre et al. |
| 5,837,278 A | 11/1998 | Geistlich et al. |
| 5,840,900 A | 11/1998 | Greenwald et al. |
| 5,891,477 A | 4/1999 | Lanza et al. |
| 5,902,110 A | 5/1999 | Alfano et al. |
| 5,902,599 A | 5/1999 | Anseth et al. |
| 5,916,585 A | 6/1999 | Cook et al. |
| 5,937,758 A | 8/1999 | Maracas et al. |
| 5,942,252 A | 8/1999 | Tice et al. |
| 5,958,911 A | 9/1999 | Evans et al. |
| 5,969,020 A | 10/1999 | Shalaby et al. |
| 6,011,042 A | 1/2000 | Greenwald et al. |
| 6,071,530 A | 6/2000 | Polson et al. |
| 6,123,956 A | 9/2000 | Baker et al. |
| 6,153,212 A | 11/2000 | Mao et al. |
| 6,171,610 B1 | 1/2001 | Vacanti et al. |
| 6,280,772 B1 | 8/2001 | Pinkus |
| 6,365,149 B2 | 4/2002 | Vyakarnam et al. |
| 6,365,172 B1 | 4/2002 | Barrows |
| 6,468,519 B1 | 10/2002 | Uhrich |
| 6,486,214 B1 | 11/2002 | Uhrich |
| 6,602,915 B2 | 8/2003 | Uhrich |
| 6,613,807 B2 | 9/2003 | Uhrich |
| 6,685,928 B2 | 2/2004 | Uhrich et al. |
| 6,689,350 B2 | 2/2004 | Uhrich |
| 7,122,615 B1 | 10/2006 | Uhrich |
| 7,396,527 B2 | 7/2008 | Uhrich |
| 7,411,031 B2 | 8/2008 | Uhrich et al. |
| 7,534,852 B2 | 5/2009 | Uhrich |
| 7,662,864 B2 | 2/2010 | Kanamathareddy et al. |
| 7,666,398 B2 | 2/2010 | Uhrich |
| 7,985,415 B2 | 7/2011 | Giroux |
| 8,017,714 B2 | 9/2011 | Uhrich |
| 8,088,405 B2 | 1/2012 | Uhrich |
| 8,221,790 B2 | 7/2012 | Uhrich |
| 8,232,322 B2 | 7/2012 | East |
| 8,241,668 B2 | 8/2012 | Uhrich |
| 8,263,060 B2 | 9/2012 | Uhrich |
| 8,361,453 B2 | 1/2013 | Uhrich et al. |
| 8,741,317 B2 | 6/2014 | Uhrich et al. |
| 8,747,832 B2 | 6/2014 | Uhrich |
| 9,108,070 B2 | 8/2015 | Kanamathareddy et al. |
| 9,144,579 B2 | 9/2015 | Uhrich et al. |
| 9,387,250 B2 | 7/2016 | Uhrich et al. |
| 2004/0038948 A1 | 2/2004 | Uhrich |
| 2004/0096476 A1 | 5/2004 | Uhrich et al. |
| 2005/0048121 A1 | 3/2005 | East et al. |
| 2005/0131199 A1 | 6/2005 | Uhrich et al. |
| 2005/0249697 A1 | 11/2005 | Uhrich et al. |
| 2006/0013851 A1 | 1/2006 | Giroux |
| 2006/0057179 A1 | 3/2006 | Giroux |
| 2007/0098800 A1 | 5/2007 | Giroux et al. |
| 2007/0196417 A1 | 8/2007 | Uhrich |
| 2010/0272670 A1 | 10/2010 | Uhrich et al. |
| 2010/0291180 A1 | 11/2010 | Uhrich |
| 2010/0291181 A1 | 11/2010 | Uhrich et al. |
| 2010/0310498 A1 | 12/2010 | Kanamathareddy et al. |
| 2013/0022569 A1 | 1/2013 | Uhrich et al. |
| 2014/0030341 A1 | 1/2014 | Uhrich et al. |
| 2016/0130211 A1 | 5/2016 | Uhrich et al. |
| 2016/0175343 A1 | 6/2016 | Uhrich et al. |

FOREIGN PATENT DOCUMENTS

| | | |
|---|---|---|
| DE | 223305 C | 5/1908 |
| DE | 227999 C | 7/1908 |
| DE | 288311 | 3/1991 |
| DE | 0288387 | 3/1991 |
| EP | 0246341 | 11/1987 |
| EP | 0498283 | 8/1992 |
| EP | 0580386 | 1/1994 |
| EP | 0764673 | 3/1997 |
| JP | 45-004740 | 2/1970 |
| JP | 51-134729 | 11/1976 |
| JP | 53-082743 | 7/1978 |
| JP | 56-007716 | 1/1981 |
| JP | 6255797 | 12/1985 |
| JP | 61186309 | 8/1986 |
| JP | 06-328857 | 11/1994 |
| JP | 07-149044 | 6/1995 |
| JP | 1036497 A | 2/1998 |
| JP | 2005-162769 | 6/2005 |
| NL | 9000237 | 8/1991 |
| WO | WO 90/09779 | 9/1990 |
| WO | WO 91/09831 | 7/1991 |
| WO | WO 97/39738 | 10/1997 |
| WO | WO 97/44016 | 11/1997 |
| WO | WO 97/49385 | 12/1997 |
| WO | WO 98/36013 | 8/1998 |
| WO | WO 99/012990 | 3/1999 |
| WO | WO 99/29885 | 6/1999 |
| WO | WO 99/36107 | 7/1999 |
| WO | WO 00/66730 | 11/2000 |
| WO | WO 01/028492 | 4/2001 |
| WO | WO 01/041753 | 6/2001 |
| WO | WO 02/009767 | 2/2002 |
| WO | WO 02/009768 | 2/2002 |
| WO | WO 02/009769 | 2/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 04/006863 | 1/2004 |
| WO | WO 04/039355 | 5/2004 |
| WO | WO 04/045549 | 6/2004 |
| WO | WO 05/039489 | 5/2005 |
| WO | WO 05/042600 | 5/2005 |
| WO | WO 06/127667 | 11/2006 |
| WO | WO 07/143698 | 12/2007 |
| WO | WO 08/034019 | 3/2008 |
| WO | WO 08/103744 | 8/2008 |
| WO | WO 08/128193 | 10/2008 |
| WO | WO 09/026544 | 2/2009 |

OTHER PUBLICATIONS

Anastasiou, T.J., "Novel Polyanhydrides with Enhanced Thermal and Solubility Properties", *Macromolecules*, 33(17), 6217-6221, (2000).

Anastasiou, T.J., "Synthesis of Novel, Degradable Polyanhydrides Containing Para-Aminosalicylic Acid as Drug Delivery Devices for Tuberculosis Treatment", *Polymer Preprints*, 41(2), 1366-1367, (Aug. 2000).

Attawia, M.A., "Biocompatibility Testing of Poly(anhydride-co-imides) Containing Pyromellitylimidoalanine", *The 21st Annual Meeting of the Society for Biomaterials*, Abstract, 222, (Apr. 5-9, 1994).

Attawia, M.A., "Cytotoxicity testing of poly(anhydride-co-imides) for orthopedic applications", *Journal of Biomedical Materials Research*, 29(10), 1233-1240, (1995).

Attawia, M.A., "In vitro bone biocompatibility of poly(anhydride-co-imides) containing pyromellitylimidoalanine", *Journal of Orthopedic Research*, 14(3), 445-454, (1996).

Attawia, M.A., "The Long Term Osteoblast Response to Poly(anhydride-co-imides): A New Degradable Polymer for Use in Bone", *Proceedings of the Fifth World Biomaterials Congress*, Toronto, Canada, 113, (1996).

Attawia, M.A., "Proliferation, Morphology, and Protein Expression by Osteoblasts Cultured on Poly(anhydride-co-amides)", *Journal of Biomedical Materials Research*, 48(3), 322-327, (1999).

Attawia, M.A., "Regional drug delivery with radiation for the treatment of Ewing's sarcoma—in vitro development of a taxol release system", *Journal of Controlled Release*, 71, 193-202 (2001).

Beaton, M.L., "Synthesis of a novel poly(anhydride-ester)", *The Rutgers Scholar—An Electronic Bulletin of Undergraduate Research*,

(56) References Cited

OTHER PUBLICATIONS 3, 1-7, (2001), http://www.scils.rutgers.edu/~weyang/ejournal/volume03/beatuhri/beatuhri.htm.
Bedell, C., "Processing and Hydrolytic Degradation of Aromatic, Ortho-Substituted Polyanhydrides", *Journal of Applied Polymer Science*, 80, 32-38, (2001).
Blandin et al., *Molec. Pharm.*, 58, 1461 (2000).
Brambley, D., et al., "Microlithography: an overview", *Advanced Materials for Optics and Electronics*, 4(2), 55-74, (Mar.-Apr. 1994).
Branch, D.W., "Microstamp patterns of biomolecules for high resolution neuronal networks", *Medical & Biological Engineering & Computing*, 36(1), 135-41, (Jan 1998).
Brown, J.P., "A Polymeric Drug for Treatment of Inflammatory Bowel Disease", *Journal of Medicinal Chemistry*, 26(9), 1300-1307, (1983).
Brown, L., et al., "Transdermal delivery of drugs", *Annual Review of Medicine*, 39, 221-9, (1988).
Cai et al., "Polyanhydride based drug containing bioadhesive polymers", Zhejiang Daxue Xuebao, Gongxueban, Abstract, 1 page (2004).
Cai et al., "Salicylic Acid and PEG-Contained Polyanhydrides: Synthesis, Characterization, and in Vitro Salicylic Acid Release", *Drug Delivery*, 12, 97-102 (2005).
Campo, C.J., "Polyanhydrides: the effects of ring substitution changes on polymer properties", *Polymer Bulletin*, 42, 61-68, (1999).
Chafi, N., "Dosage Form with Salicylic Acid Attached to the Polyanhydride Polymer Dispersed in an Eudragit Matrix", *International Journal of Pharmaceutics*, 52, 203-211, (1989).
Chatterjee, R., et al., "Mechanism for the Increase in Solubility of Deoxyhemoglobin S due to Cross-Linking the Beta Chains Between Lysine-82 Betal and Lysine-82 Beta 2", *Biochemistry*, 21, 5901-5909, (1982).
Chemical Abstract Search, Beilstein Record No. 3499573, 1 page.
Chemical Abstract Search, Beilstein Record No. 3177399, 1 page.
Chen, G., "Effect of protein and cell behavior on pattern-grafted thermoresponsive polymer", *Journal of Biomedical Materials Research*, 42(1), 38-44, (Oct. 1998).
Conix, A., "New High-Melting Fibre-Forming Polymers", *Die Makromolekulare Chemie*, XXIV, 76-78, (1957).
Conix, A., "Aromatic Polyanhydrides, a New Class of High Melting Fiber-Forming Polymers", *Journal of Polymers Science*, XXIX, 343-353, (1958).
Conix, A., "Poly [1,3-bis (p carboxyphenoxy)—Propane anhydride]", *Macromolecular Synthesis*, 2, 95-99, (1996).
Davaran, S., "Release of 5-amino Salicylic Acid from Acrylic Type Polymeric Prodrugs Designed for Colon-specific Drug Delivery", *Journal of Controlled Release*, 58(3), 279-287, (1999).
Davies, M.C., "The Analysis of the Surface Chemical Structure of Biomedical Aliphatic Polyanhydrides Using SPX and ToF-SIMS", *Journal of Applied Polymer Science*, 42, No. 6, New York, US, 1597-1605, (Mar. 20, 1991).
Delamarche, E., et al., "Patterned delivery of immunoglobulins to surfaces using microfluidic networks", *Science*, 276(5313), 779-781, (May 2, 1997).
Delaney, E.J. et al., "Alternative Diaspirins for Modification of Hemoglobin and Sickle Hemoglobin", Archives of Biochemistry and Biophysics, 228(2), 627-638 (1984).
Dewez, J.L., et al., "Adhesion of mammalian cells to polymer surfaces: from physical chemistry of surfaces to selective adhesion on defined patterns", *Biomaterials*, 19(16), 1441-1445, (Aug. 1998).
Domb, A.J., "Polyanhydrides. I. Preparation of High Molecular Weight Polyanhydrides", *Journal of Polymer Science: Part A: Polymer Chemistry*, 25, 3373-3386, (1987).
Domb, A.J., "Synthesis and Characterization of Biodegradable Aromatic Anhydride Copolymers", *Macromolecules*, 25, 12-17, (1992).
Dontha, N., "Generation of biotin/avidin/enzyme nanostructures with maskless photolithography", *Analytical Chemistry*, 69(14), 2619-25, (Jul. 15, 1997).

Dukovic, G., "Novel degradable poly(anhydride-esters) for controlled drug release", *The Rutgers Scholar—An Electronic Bulletin of Undergraduate Research*, 1, 1-10, (1999), http://www.scils.rutgers.edu/~weyang/ejournal/volume01/uhriduko/uhriduko.htm.
Erdmann, L., "Polymer Prodrugs with Pharmaceutically Active Degradation Products", *Polymer Preprints*, 38(2), 570-571, (1997).
Erdman et al., "Synthesis and Characterization of a Polymeric Prodrug", *Proceedings of the American Chemical Society Division of Polymeric Materials: Science and Engineering*, 78, Abstract Spring Meeting, Dallas, TX, pp. 194, (Apr. 1998).
Erdmann, L., et al., Chapter 5, "Polymeric Prodrugs: Novel Polymers with Bioactive Components", *In: Tailored Polymeric Materials for Controlled Delivery Systems*, I. McCulloh, et al., (Editors), ACS Symposium Series 709, Developed from a symposium sponsored by the Division of Polymer Chemistry at the 214th National Meeting of the American Chemical Society, Las Vegas, Nevada, Sep. 7-11, 1997, American Chemical Society: Washington, D.C., 83-91, (1998).
Erdmann, L., "Polymeric Prodrugs: Novel Polymers for Delivery of Salicylic Acid", *Annals of Biomedical Engineering*, 26 (*Suppl. 1*), Abstract No. PB.26, Annual Fall Meeting, S-124, (1998).
Erdmann, L., "Polymeric Salicylic Acid: in Vitro and in Vivo Degradation", *Polymer Preprints*, 39(2), 224-225, (1998).
Erdmann, L., "Degradable poly(anhydride ester) implants: effects of localized salicylic acid release on bone", *Biomaterials*, 21(24), 2507-2512, (2000).
Erdmann, L., "Synthesis and degradation characteristics of salicylic acid-derived poly(anhydride-esters)", *Biomaterials*, 21(19), 1941-1946, (Oct. 2000).
Fukushima, Yoshitaka (Examiner), Office Action issued by the Japanese Patent Office and English language summary, dated Nov. 30, 2010, 9 pages.
Giammona, G., "Polymeric Prodrugs alpha beta poly-hyroxyethyl-d1-aspartamide as macromolecular carrier for some non-steroidal anti-inflammatory agents", *Abstracts from Database BIOSIS Online, Biosciences Information Services*, Philadelphia, PA, Original Publication from the International Journal of Pharmaceutics (Amsterdam), 1 page (1989).
Giammona, G., "Polymeric Prodrugs Alpha Beta Poly-N-hydroxyethyl-DL-aspartamide as a Macromolecular Carrier for Some Non-Steroidal Anti-inflammatory Agents", *International Journal of Pharmaceutics*, 57, 55-62, (1989).
Giessen et al., "Marked Inflammatory Sequelae to Implantation of Biodegradable and Nonbiodegradable Polymers in Porcine Coronary Arteries", *Circulation*, vol. 94 (7), 1690-1697 (1996).
Gouin, S., et al., "New Polyanhydrides Made from a Bile Acid Dimer and Sebacic Acid: Synthesis, Characterization and Degradation", *Macromolecules*, 33, 5379-5383, (2000).
Gunn et al., "Stent Coatings and Local Drug Delivery", *European Heart Journal*, 20, 1693-1700 (1999).
Herbert, C.B., "Micropatterning gradients and controlling surface densities of photoactivatable biomolecules on self-assembled monolayers of oligo(ethylene glycol) alkanethiolates", *Chemistry & Biology*, 4(10), 731-7, (Oct. 1997).
Hicks et al., "Composition dependant in-vitro release kinetics from polyNSAIDs through the copolymer design for a new class of ester-anhydride polymers", *PMSE Preprints*, 92, 26-27 (2005).
Ibim, S., "Controlled Release Based on Poly(anhydride-co-imides)", *Proc. Intern. Symp. Control. Rel. Bioact. Mater.*, 22, 2 pgs, (1995).
Ibim, S.M., "Poly(anhydride-co-imides): in Vivo Biocompatibility in a rat model", *Biomaterials*, 19(10), 941-951, (1998).
Ibim, S.E., "Preliminary in vivo report on the osteocompatibility of poly(anhydride-co-imides) evaluated in a tibial model.", *Journal of Biomedical Material Research*, 43(4), 374-379, (Winter 1998).
Ito, Y., "Micropatterned immobilization of epidermal growth factor to regulate cell function", *Bioconjugate Chemistry*, 9(2), 277-82, (Mar.-Apr. 1998).
James, C.D., "Patterned Protein Layers on Solid Substrates by Thin Stamp Microcontact Printing", *Langmuir*, 14(4), 741-744, (1998).

(56) References Cited

OTHER PUBLICATIONS

Jiang, H.L., "Synthesis, Characterization and in Vitro Degradation of a New Family of Alternate Poly(ester-anhydrides) Based on Aliphatic and Aromatic Diacids", *Biomaterials*, 22(3), 211-218, (2001).
Johnson et al., "Accelerated deacylation of acyl salicylates and neighboring group effects in derivatives of poly(ethylenimine)", *Biopolymers*, 18(2), 313-325 (1979).
Jucker, M., et al., "Fetal rat septals cells adhere to and extend processes on basement membrane, laminin, and a synthetic peptide from the laminin A chain sequence", *Journal of Neuroscience Research*, 28(4), 507-17, (Apr. 1991).
Kleinfeld, D., "Controlled outgrowth of dissociated neurons on patterned substrates", *Journal of Neuroscience*, 8(11), 4098-120, (Nov. 1998).
Krogh-Jespersen, E., "Synthesis of a Novel Aromatic Polyanhydride Containing Aminosalicylic Acid", *Polymer Preprints*, 41(1), 1048-1049, (2000).
Kwansa et al., "Adipyl crosslinked bovine hemoglobins as new models of allosteric systems", *Proteins: Structure, Function, and Genetics*, 39(2), 166-169 (2000).
Langer, R., "New Methods of Drug Delivery", *Science*, 249(4976), 1527-1533, (Sep. 1990).
Laurencin, C.T., "The Bone Biocompatibility of Poly(anhydride-co-imides)—A new generation degradable Polymer for Orthopedic Applications", 41st Annual Meeting of the Orthopedic Research Society, Orlando, FL, 143-24, (1995).
Laurencin, C.T., "Poly(anhydrides-co-imides): in Vivo Biocompatibility Study", *23rd Annual Meeting of the Society for Biomaterials*, New Orleans, LA, 483, (1997).
Laurencin, C.T., "The Biocompatibility of Poly(anhydride-co-imides): High Strength Polymers for Controlled Drug Delivery", *Proc. 24th Int'l Symp. Control. Rel. Bioact. Mater.*, 973-974, (1997).
Laurencin, et al., "The controlled delivery of radiosensitizers: taxol treatment for Ewing Sarcoma", *Proceedings of the 25$^{th}$ Int'l Symp. Control. Rel. Bioact. Mater.*, pp. 236-237, (1998).
Longer, M.A., "Sustained-Release Drug Delivery Systems", *Remington's Pharmaceutical Sciences*, 18th Edition, Chapter 91, 1676-1693, (1990).
Macedo, B., et al., "The in vivo Response to a Bioactive Biodegradable Polymer", *Journal of Dental Research*, 78, Abstract No. 2827, 459, (1999).
Macedo, B., "The in Vivo Response to Bioactive Polyanhydride Monofilament", *Journal of Dental Research*, 79 (*Abstract No.* 3872), 627, (2000).
Namazi et al., "Synthesis of polyfunctional dendrimeric type copolymer as the hydrogels and investigation of their thermoreversible behaviors", HCAPLUS Accession No. 2006:93046, *Iranian Polymer Journal*, 14(11), English Abstract (2005).
O'Sullivan, Paul, (Examiner), Extended European Search Report, dated Feb. 17, 2011, 8 pages.
Patent Cooperation Treaty, International Searching Authority, Search Report and Written Opinion for PCT/US2007/78426, 10 pages, dated Apr. 8, 2008.
Pinther, P., "Synthesis of Polyanhydrides Containing Ester Groups", *Die Makromolekulare Chemie, Rapid Communications*, 11(8), 403-408, (Aug. 1990).
Prudencio et al., "Effect of Linker Structure on Salicylic Acid-Derived Poly(anhydride-esters)", *Macromolecules*, 38(16), 6895-6901 (2005).
Reynolds, et al., "Non-steroidal anti-inflammatory drug (NSAID)-derived poly(anhydride-esters) in bone and periodontal regeneration", *Current Drug Delivery*, 4(3), 233-239 (Jan. 1, 2007).
Schacht, E., "Polymers for Colon Specific Drug Delivery", *Journal of Controlled Release*, 39, 327-338, (1996).
Schmalenberg, K., "Microlithographic patterning of polymer substrates for directed neuronal", *Polymeric Materials Science Engineering*, 81, *Fall Meeting*, Aug. 22-26, 1999, New Orleans, LA., 97, (1999).

Schmalenberg, K., "Patterned Polymer Substrates for directing Neuronal Growth", *ACS Regional Mid-Atlantic Research Meeting*, (1999).
Schmalenberg, K., "Patterning of polymer substrates for directed neuronal growth studies", *Laboratory for Surface Modification*, (Mar. 18, 1999).
Schmalenberg, K., "Thin Stamp Microcontact Patterned Printing of Protein Layers on Polymer Substrates", *Transactions: Twenty-Fifth Annual Meeting of the Society for Biomaterials*, Apr. 28-May 2, (1999).
Seidel, J.O., "Erosion of Poly(anhydride-co-imides): A Preliminary Mechanistic Study", *J. Appl. Polym. Sci.*, 62(8), 1277-1283, (1996).
Shen, E., "Morphological Characterization of Erodible Polymer Carriers for Drug Release", *Proc. 26th Int'l Symp. Control. Rel. Bioact. Mater.*, 717-718, (1999).
Spargo, B.J., et al., "Spatially controlled adhesion, spreading, and differentiation of endothelial cells on self-assembled molecular monolayers", *Proceedings of the National Academy of Science USA*,91(23), 11070-11074, (Nov. 8, 1994).
St. John, P.M., "Diffraction-based cell detection using a microcontact printed antibody grating", *Analytical Chemistry*, 70(6), 1108-11, (Mar. 15, 1998).
Stuart, M., "Technology Strategies, Stent and Deliver", *Start-Up, Windhover's Review of Emerging Medical Ventures*, 34-38 (2000).
Tashiro, K., et al., "A synthetic peptide containing the IKVAV sequence from the A chain of laminin mediates cell attachment, migration, and neurite outgrowth", *Journal of Biological Chemistry*, 264(27), 16174-82, (Sep. 25, 1989).
Uhrich, K.E., "Synthesis and Characterization of poly(anhydride co-imides): Solution Polycondensation of Biodegradable Polymers Derived from Amino Acids", *Proc. of the American Chemical Society, Division of Polymeric Materials: Science and Engineering*, 70, Spring Meeting, San Diego, CA, 239-240, (1994).
Uhrich, K.E., "Synthesis and Characterization of Degradable poly(anhydride-co-imides)", *Macromolecules*, 28(7), 2184-2193, (1995).
Uhrich, K.E., "Degradation of poly(anhydride-co-imides): Novel Polymers for Orthopedic Applications", *Mat. Res. Soc. Symp. Proc.*, 394, 41-46, (1995).
Uhrich, K.E., "In Vitro Degradation Characteristics of Poly(anhydride-imides) Containing Pyromellitylimidoalanine", *J. Appl. Polymer Sci., Part A, Polym. Chem.*, 34(7), 1261-1269, (1996).
Uhrich, K.E., "In Vitro Degradation Characteristics of Poly(anhydride-imides) Containing trimellitylimidoglycine", *J. Appl. Polymer. Sci.*, 63(11), 1401-1411, (1997).
Uhrich, K.E., "Chemical Changes during in vivo degradation of poly(anhydride-imide) matrices", *Biomaterials*, 19(22), 2045-2050, (1998).
Uhrich, K.E., "Poly(anhydride-ester) Degradation: Mechanical Changes and Correlation to Antibiotic Release", *American Chemical Society, Abstracts of Papers, Part 2, Abstract* No. 121, 221$^{st}$ ACS National Meeting, San Diego, CA, Abstract 121, (2001).
Uhrich, K.E., "Synthesis of Aminosalicylate-based polyanhydride Prodrugs: Esters, Amides, and Azos", *American Chemical Society, Abstracts of Papers, Part 2, Abstract* No. 407, 222nd ACS National Meeting, Chicago, IL, Abstract 407, (2001).
Walder et al., "Development of antisickling compounds that chemically modify hemoglobin S specifically within the 2, 3-diphosphoglycerate binding site", *Journal of Molecular biology*, 141(2), 195-216 (1980).
Weinberg, E.D., "The mutual effects of antimicrobial compounds and metallic cations", *Bacteriol Rev* 21 (1), 46-68 (1957).
Woo et al., "Synthesis and characterization of a novel biodegradable antimicrobial polymer", *Biomaterials*, 21, 1235-1246 (2000).
Woo, G.L., "Biological Characterization of a Novel Biodegradable Antimicrobial Polymer Synthesized with Fluoroquinolones", *J. Biomed. Mater. Res.* 59, 35-45, (2002).
Wood et al., "Structural specificities in acylation of hemoglobin and sickle hemoglobin by diaspirins", *J. Biol. Chem.*, 256 (13), 7046-7052 (1981).
Yazdi et al., "Effects of non-steroidal anti-inflammatory drugs on demineralized bone-induced bone formation", *Journal of Periodontal Research*, 27(1), 28-33, (Jan. 1992).

(56) References Cited

OTHER PUBLICATIONS

Yoda, N., "Synthesis of polyanhydrides. XII. Crystalline and high melting polyamidepolyanhydride of methylenebis(p-carboxybhenyl)amide", *Journal of Polymer Science*, 1, 1323-1338, (1963).
Zaugg, R.H., et al., "Modification of Hemoglobin with Analogs of Aspirin", *The Journal of Biological Chemistry*, 255(7), 2816-2821, (1980).

\* cited by examiner

Cumulative Percent Release of Salicylic Acid Over Time
From Example 1

Cumulative Percent Release of Salicylic Acid Over Time
From Comparative Example 1

ACTIVE AGENTS AND THEIR OLIGOMERS AND POLYMERS

RELATED APPLICATION

This application is a continuation of U.S. Ser. No. 13/467,623, filed on May 9, 2012, now U.S. Pat. No. 9,108,070, which is a continuation of U.S. Ser. No. 12/813,776, filed on Jun. 11, 2010, now abandoned, which is a continuation of U.S. Ser. No. 12/441,347, filed Mar. 13, 2009, now abandoned, which is a 35 U.S.C. § 371 application of International Application No. PCT/US2007/078426, filed Sep. 13, 2007, which claims priority under 35 U.S.C. 119(e) to provisional application U.S. Ser. No. 60/825,465, filed Sep. 13, 2006, which applications are incorporated herein by reference in their entireties.

This invention relates to conjugates comprising active agents linked together by a diglycolic acid or polyglycol diacid linker, preferably attached to the active agents at hydroxyl groups on the active agent. The invention also concerns oligomers and polymers of these conjugates. Optionally, the active agents may further contain one or more carboxylic acid groups, which are particularly useful as sites for polymerization of the conjugates. The inventive conjugates and polymers release their active agents over a desirable period of time when applied to a desired site for use. Active agents include therapeutic agents and agents for industrial applications, such as fungicides, pesticides, and anti-microbial agents, which can be applied to a desired surface for localized delivery of the active agent over a desired period of time.

BACKGROUND

Active agents, specifically therapeutic agents, conjugated to biocompatible linkers and their use in forming the backbone of polymeric drug delivery systems are known. For example, U.S. Pat. No. 6,486,214 to Uhrich discloses the tethering of two drug molecules via an aliphatic linker and the subsequent polymerization of these compositions through the formation of anhydride linkages between the drug moieties. In Uhrich, the moiety that connects the aliphatic linker to the drug molecule is an amide, thioamide, ester or thioester group. Uhrich further discloses that these polyanhydrides may be used as vehicles for the clinical delivery of the linked drug upon degradation of the polymer to its drug and biocompatible linker components.

Other aliphatic linkers have been disclosed in Australian Patent No. 750,424 to Uhrich, U.S. App. Pub. No. 20050131199 A1 and U.S. App. Pub. No. 20050048121 A1. In addition to aliphatic linkers, AU 750,424 discloses in general terms linkers with a backbone of an alkylene group having one to twenty carbon atoms and linkers with a backbone of two to twenty carbon atoms having a structure selected from (—CH$_2$—CH$_2$—O—)$_m$, (—CH$_2$—CH$_2$—CH$_2$—O—)$_m$, and (—CH$_2$—CHCH$_3$—O—)$_m$. In addition to aliphatic linkers, U.S. App. Pub. Nos. 20050131199 A1 and 20050048121 A1 disclose in general terms linkers where one or more of the carbon atoms of the aliphatic chain linker are substituted with one or more oxygen or nitrogen atoms. The therapeutic agent-linker conjugates of these applications are used as monomers to form oligomeric and polymeric drug delivery compositions.

U.S. Pat. No. 5,840,900 to Greenwald et al. discloses the use of a substantially non-antigenic polymer as a linker to form a drug-linker prodrug. The backbones of these linkers are polyalkylene oxide derivatives, preferably polyethylene glycol derivatives having a molecular weight above 20,000 Daltons. Further polymerization of these conjugates is not taught.

U.S. App. Pub. No. 20050048121 A1 discloses copolymers of aliphatically-linked diflunisal monomers with either lactate or glycolate diol co-linkers, which contain the α-hydroxy carboxylic acid ester functionality, for use as vehicles to deliver diflunisal upon degradation. German patents DE 223305 and DE 227999 disclose diglycolic acid-linked salicylic acid. DE 227999 discloses that it can be used therapeutically to overcome the stomach-irritating effects of salicylic acid alone while maintaining potency. DE 223305 teaches that the compounds are useful as medicaments. In addition, Greenwald discloses in general terms the conjugation of its polymer linkers to a drug via α-hydroxy carboxylic acid ester groups, among others. However, Greenwald also teaches that the degradation rate of its prodrugs depends not only the type of linking moiety used, but also on whether the polymer linker possesses sufficiently high molecular weight.

EMBODIMENTS OF THE INVENTION

An embodiment of the present invention is a compound according to formula (I):

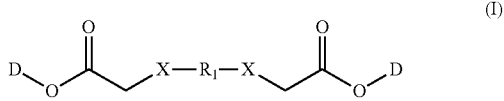

wherein
each D is the same or different and is an active agent, such as a therapeutic agent,
R$_1$ is selected from the group consisting of —[(CH$_2$)$_x$O]$_y$(CH$_2$)$_z$—, —(CH$_2$)$_y$—, —[CH=CH—O]$_y$(CH$_2$)$_z$, —[(CH=CH—CH$_2$—O]$_y$(CH$_2$)$_z$—, —[CH$_2$—CH=CH—O]$_y$(CH$_2$)$_z$—, —[(CH$_2$)$_x$O]$_y$(CH=CH)—,
preferably —(CH$_2$CH$_2$O)$_y$(CH$_2$)$_z$— or —(CH$_2$)—,
wherein w is 1 or 2,
x is 2 or 3, and
y is equal to an integer from 1 to 10, from 1 to 4, or from 1 to 3,
z is equal to 1 or 2, and
the carbon atoms of R$_1$ may be optionally substituted with substituents selected from the group consisting of C$_1$ to C$_{12}$ alkyl, C$_1$ to C$_{12}$ alkoxy, C$_3$ to C$_{12}$ cycloalkyl, C$_3$ to C$_{12}$ cycloalkoxy, C$_1$ to C$_{12}$ alkanoyl, C$_1$ to C$_{12}$ alkanoyloxy, C$_1$ to C$_{12}$ alkoxy carbonyl, C$_1$ to C$_{12}$ alkylthio, azido, cyano, nitro, fluoro, chloro, bromo, iodo, hydroxy, oxo, carboxy, aryl, aryloxy, heteroaryl, and heteroaryloxy;
each X is the same or different and is selected from the group consisting of —O—, —NR$_2$—, —S—, —SO—, and —SO$_2$—, preferably —O—, —NR$_2$—, and —S—, more preferably —O— and —NR$_2$— and most preferably —O—,
wherein R$_2$ is an alkyl group of 1 to 12 carbon atoms, preferably an alkyl group of 1 to 4 carbon atoms or of 1 to 2 carbon atoms, and most preferably a methyl group.

Another embodiment of the present invention is a compound comprising a unit of the formula (II):

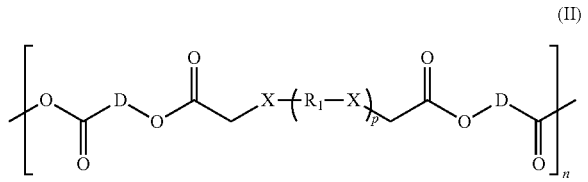

(II)

wherein
n is a positive integer;
p is 0 or 1;
each D is the same or different and is an active agent, such as a therapeutic agent,
$R_1$ is selected from the group consisting of —[(CH$_2$)—O]$_y$(CH$_2$)$_z$—, —(CH$_2$)$_y$—, —[CH=CH—O]$_y$(CH$_2$)$_z$—, —[(CH=CH—CH$_2$—O]$_y$(CH$_2$)$_z$—, —[CH$_2$—CH=CH—O]$_y$(CH$_2$)$_z$, —[(CH$_2$)$_x$O]$_y$(CH=CH)—, preferably —(CH$_2$CH$_2$O)$_y$(CH$_2$)$_z$— or —(CH$_2$)—,
wherein w is 1 or 2,
x is 2 or 3,
y is equal to an integer from 1 to 10, from 1 to 4, or from 1 to 3,
z is equal to 1 or 2, and
the carbon atoms of $R_1$ may be optionally substituted with substituents selected from the group consisting of $C_1$ to $C_{12}$ alkyl, $C_1$ to $C_{12}$ alkoxy, $C_3$ to $C_{12}$ cycloalkyl, $C_3$ to $C_{12}$ cycloalkoxy, $C_1$ to $C_{12}$ alkanoyl, $C_1$ to $C_{12}$ alkanoyloxy, $C_1$ to $C_{12}$ alkoxy carbonyl, $C_1$ to $C_{12}$ alkylthio, azido, cyano, nitro, fluoro, chloro, bromo, iodo, hydroxy, oxo, carboxy, aryl, aryloxy, heteroaryl, and heteroaryloxy;
each X is the same or different and is selected from the group consisting of —O—, —NR$_2$—, —S—, —SO—, and —SO$_2$—, preferably —O—, —NR$_2$—, and —S—, more preferably —O— and —NR$_2$— and most preferably —O—,
wherein $R_2$ is an alkyl group of 1 to 12 carbon atoms, preferably an alkyl group of 1 to 4 carbon atoms or of 1 to 2 carbon atoms, and most preferably a methyl group provided that, when p is 0, n is not 1.

Another embodiment of the present invention is a polyanhydride comprising the compound of formula (II), wherein n is equal to an integer from 2 to 100 or from 2 to 20.

Another embodiment of the present invention comprises a compound of formula (III):

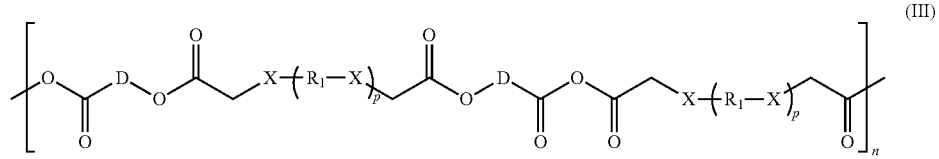

wherein
n is a positive integer;
p is the same or different and is 0 or 1;
each D is the same or different and is an active agent, such as a therapeutic agent,
$R_1$ is the same or different and is selected from the group consisting of —[(CH$_2$)$_x$O]$_y$(CH$_2$)$_z$—, —(CH$_2$)$_y$—, —[CH=CH—O]$_y$(CH$_2$)$_z$—, —[(CH=CH—CH$_2$—O]$_y$(CH$_2$)$_z$—, —(CH$_2$—CH=CH—O)$_y$(CH$_2$)$_z$—, —[(CH$_2$)$_x$O]$_y$(CH=CH)—,
preferably —(CH$_2$CH$_2$O)$_y$(CH$_2$)$_z$ or —(CH$_2$)—,
wherein w is 1 or 2,
x is 2 or 3,
y is equal to an integer from 1 to 10, from 1 to 4, or from 1 to 3,
z is 1 or 2, and
the carbon atoms of $R_1$ may be optionally substituted with substituents selected from the group consisting of $C_1$ to $C_{12}$ alkyl, $C_1$ to $C_{12}$ alkoxy, $C_3$ to $C_{12}$ cycloalkyl, $C_3$ to $C_{12}$ cycloalkoxy, $C_1$ to $C_{12}$ alkanoyl, $C_1$ to $C_{12}$ alkanoyloxy, $C_1$ to $C_{12}$ alkoxy carbonyl, $C_1$ to $C_{12}$ alkylthio, azido, cyano, nitro, halo, hydroxy, oxo, carboxy, aryl, aryloxy, heteroaryl, and heteroaryloxy;
each X is independently selected from the group consisting of —O—, —NR$_2$—, —S—, —SO—, and —SO$_2$—, preferably —O—, —NR$_2$—, and —S—, more preferably —O— and —NR$_2$— and most preferably —O—,
wherein $R_2$ is an alkyl group of 1 to 12 carbon atoms, preferably an alkyl group of 1 to 4 carbon atoms or of 1 to 2 carbon atoms, and most preferably a methyl group.

Another embodiment of the present invention is a composition comprising an effective amount of a compound according to the invention, such as of formula (I), (II) and/or (III), and a vehicle. In one embodiment, the composition is a pharmaceutical composition comprising a therapeutically effective amount of the compound of the invention and a pharmaceutically acceptable vehicle.

Methods of using the inventive compositions, such as therapeutic treatment by administering effective amounts of the composition to a mammal in need thereof and industrial applications such as applying effective amounts of the composition to a surface where the activity of the active agent is desired, are also included in the invention.

Another embodiment of the present invention is a composition for topical use such as for acne treatment or bandage coating comprising a pharmaceutically acceptable vehicle such as a surfactant and a therapeutically effective amount of a compound having the formula:

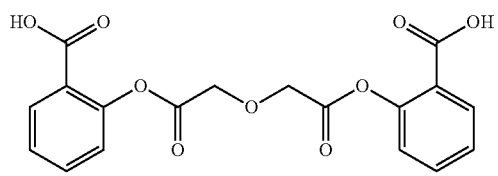 [SMILES: O=C(COCC(=O)Oc1ccccc1C(=O)O)Oc1ccccc1C(=O)O]

DETAILED DESCRIPTION

Figure 1:
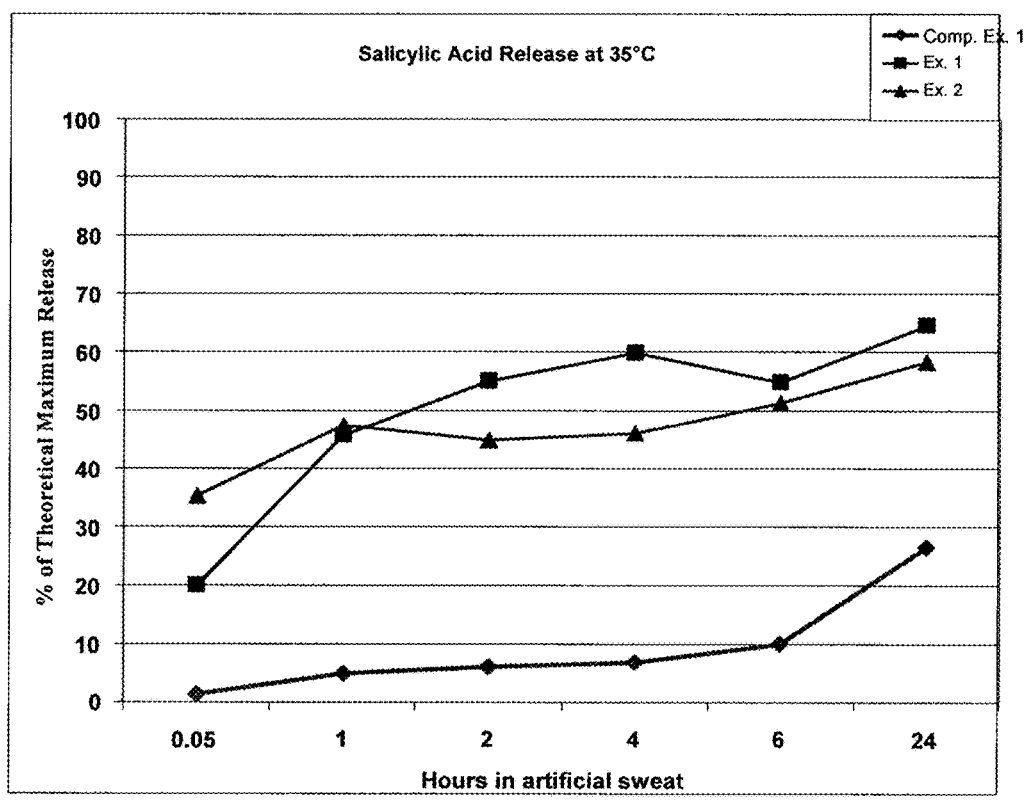
FIG. 1 illustrates salicylic acid release at 35° C. Samples of Example 1 (square), Example 2 (triangle) and Comparative Example 1 (diamond) were placed in artificial sweat or artificial sweat plus proteins and incubated at 35° C. for 3 to 5 minutes, 1, 2, 4, 6 and 24 hours, rapidly filtered (0.22 μm filter) and analyzed for salicylic acid by HPLC.

The compounds and compositions thereof of the invention have desirable degradation properties under normal conditions of use such that the active agent in the compound or composition is released at the desired site over a suitable period of time. The inventive compounds comprise two active agents conjugated to each other by a linker, preferably attached to them via hydroxyl groups on the active agents such that an ester bond is formed between the active agent and linker. The linkers are biocompatible diglycolic acid or polyglycol diacid linkers and derivatives thereof. The rapid elution profiles of these compounds make them useful, inter alia, in topical applications such as personal care products, cosmetics, dressings and wound care and to form or coat devices, and other uses where it is desired for the active agent to be released over a period of time such as within from less than about 1 hour to about 48 hours or desirable to have a site specific administration of the active agent in a composition that is convenient for administration. Longer release rates can also be achieved. The present invention is also directed to novel oligomers and polymers of the compounds of the invention.

As used herein, the term "active agent" is a compound having a useful activity, particularly when administered over time and/or administered topically to a surface. The useful activity may be for a therapeutic use, such as for medical treatment of a condition or disorder, or an industrial use, such as preventing microbial growth in a surface coating such as paint. In one embodiment, the active agent is a therapeutically active compound. By therapeutically active compound is meant a compound that upon effective dosage to a mammal can treat, prevent or ameliorate symptoms of a disease or medical condition. Preferred as active agents are low molecular weight (10000 daltons or less) drugs that have pharmacological activity. Examples of preferred active agents are salicylic acid and diflunisal. Low molecular weight drugs can also be useful in industrial applications, such as the application of compounds of the invention comprising anti-microbial agents to liquid coatings and other liquid formulations to prevent microbial growth. Preferably the active agent has a molecular weight of 1200 or less, 1000 or less, or 900 or less. Examples of suitable active agents are provided below.

As used herein, the active agent or "D" in formulas I, II and III has a hydroxyl group prior to formation of the compounds of the invention. The active agent forms an ester bond with a linker through reaction at the hydroxyl group of the active agent with the carboxylic acid group of the linkers disclosed herein. The active agent also may contain at least one aryl group, preferably a phenyl group, and preferably the active hydroxyl group is attached directly to the aryl group. As used herein, the term "aryl" denotes a phenyl radical or an ortho-fused bicyclic carbocyclic radical having about nine to ten ring atoms in which at least one ring is aromatic or a heteroaryl. As used herein, the term "heteroaryl" encompasses a radical attached via a ring carbon of a monocyclic aromatic ring containing five or six ring atoms consisting of carbon and one to four heteroatoms each selected from the group consisting of non-peroxide oxygen, sulfur, and N(X), wherein X is absent or is H, O, $C_1$ to $C_6$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

In the polymers and oligomers of the invention, the active agent contains a carboxylic acid group in additional to the hydroxyl group prior to formation of the inventive polymer or oligomer. The active agent forms a polyanhydride bond with a linker or another active agent through reaction of the carboxylic acid on the active agent with a carboxylic acid on the linker or on the other active agent.

The linkers of the present invention are based on diglycolic acid and polyglycol diacids. The structures of diglycolic acid and polyglycol diacids are as follows:

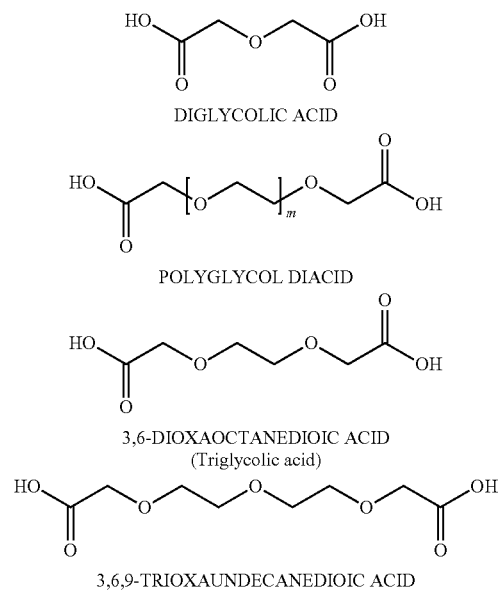

In the case of polyglycol diacids, when m equals 1, the polyglycol diacid is 3,6-dioxaoctanedioic acid ("triglycolic acid") and when m equals 2, the polyglycol diacid is 3,6,9-trioxaundecanedioic acid. These linkers are more hydrophilic in character than their aliphatic equivalents as a result of the incorporation of oxygen into the linker backbone. These linkers form α-hydroxy carboxylic acid ester moieties when conjugated with active agents containing at least one hydroxyl group. As used herein, the structure of an α-hydroxy carboxylic acid ester moiety is defined as:

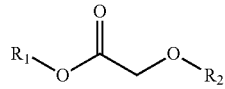

wherein $R_1$ and $R_2$ are not hydrogen. This combination of features increases the rate of hydrolytic degradation of active agent-linker conjugates (monomers), oligomers, and polymers containing these linkers when compared to such compositions containing aliphatic linkers, resulting in faster release of the active agent.

Use of aliphatic linkers as in the background references discussed above may result in an undesirably slow rate of degradation for particular applications. This is believed to be attributable to their relative hydrophobicity, resulting in a slower rate of hydrolysis of the bond between the linker and the active agent. Hydrophilicity of the linker may be increased by substituting one or more of the carbon atoms of the aliphatic chain of the linker with one or more oxygen atoms. Without limiting the invention in any way, it is believed that the rate of hydrolysis of these linkers is enhanced due to increased hydrogen bonding capability.

The invention includes compounds of the general structure D-L-D where D is an active agent and L is a diglycolic acid or polyglycol diacid linker or derivatives thereof such as the compounds of the formula (I) as defined above. Another embodiment of the present invention is a compound having the formula:

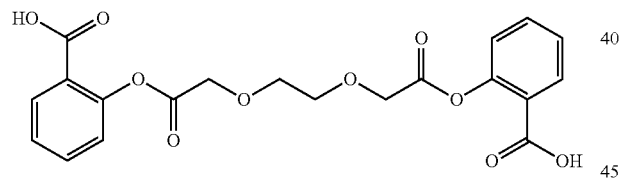

Another embodiment of the present invention is a compound having the formula:

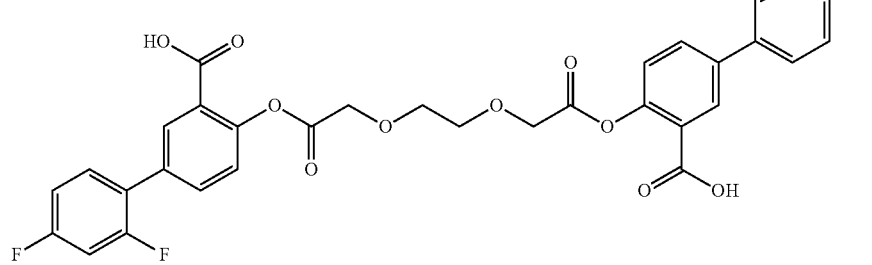

Another embodiment of the present invention is a polyanhydride having the formula:

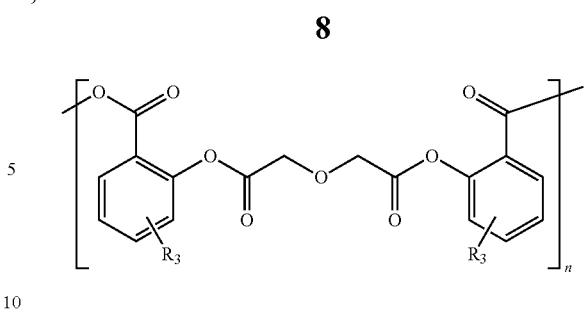

wherein n is a positive integer greater than 1, such as from 2 to 10, equal to 3 or equal to 4, and wherein $R_3$ is selected from the group consisting of —H, —CF$_3$, —F, —Cl, —Br, —I, —OH, —NH$_2$, —NO$_2$, —CN, $C_1$ to $C_{12}$ straight-chain or branched alkyl, $C_1$ to $C_{12}$ alkoxy, $C_3$ to $C_{12}$ cycloalkyl, $C_3$ to $C_{12}$ cycloalkoxy, $C_1$ to $C_{12}$ alkanoyl, $C_1$ to $C_{12}$ alkanoyloxy, $C_1$ to $C_{12}$ alkoxy carbonyl, $C_1$ to $C_{12}$ alkylthio, azido, oxo, carboxy, aryl, aryloxy, heteroaryl, heteroaryloxy, and the following structures:

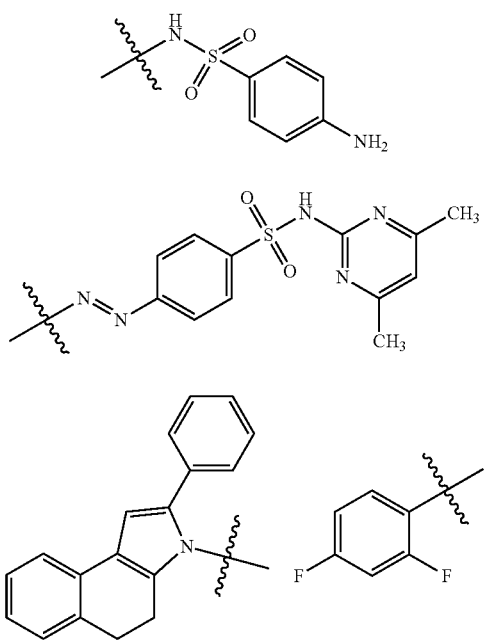

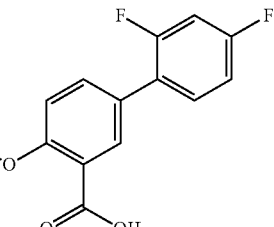

Another embodiment of the present invention is a polyanhydride having the formula:

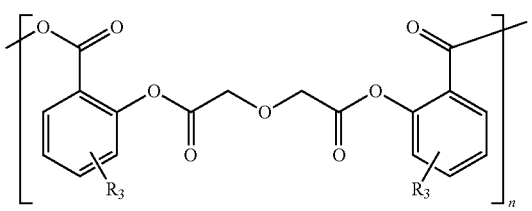

wherein n is a positive integer greater than 1 and wherein R₃ is

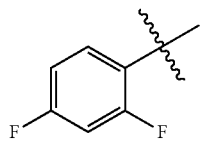 [SMILES: *c1ccc(F)cc1F]

Another embodiment of the present invention is a polyanhydride having the formula:

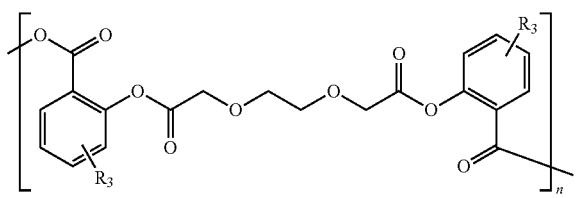

wherein n is a positive integer greater than 1 such as from 2 to 10, equal to 3 or equal to 4, and R₃ is selected from the group consisting of —H, —CF₃, —F, —Cl, —Br, —I, —OH, —NH₂, —NO₂, —CN, $C_1$ to $C_{12}$ straight-chain or branched alkyl, $C_1$ to $C_{12}$ alkoxy, $C_3$ to $C_{12}$ cycloalkyl, $C_3$ to $C_{12}$ cycloalkoxy, $C_1$ to $C_{12}$ alkanoyl, $C_1$ to $C_{12}$ alkanoyloxy, $C_1$ to $C_{12}$ alkoxy carbonyl, $C_1$ to $C_{12}$ alkylthio, azido, oxo, carboxy, aryl, aryloxy, heteroaryl, heteroaryloxy, and the following structures:

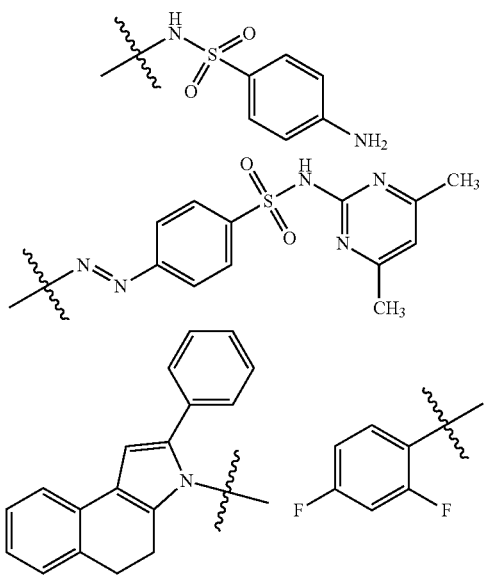

Another embodiment of the present invention is a polyanhydride having the formula:

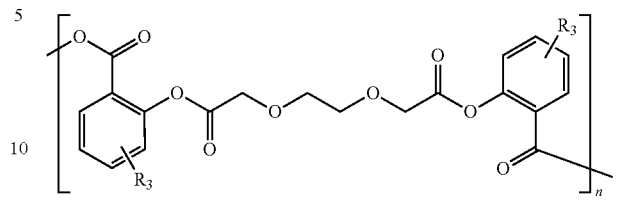

wherein n is a positive integer greater than 1 and wherein R₃ is —H.

Another embodiment of the present invention is a polyanhydride having the formula:

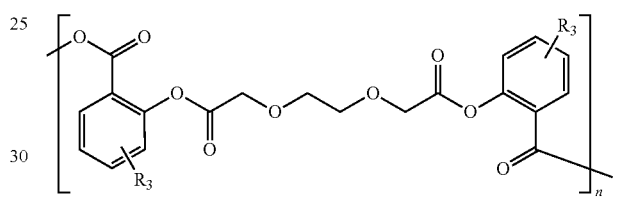

wherein n is a positive integer greater than 1 and wherein R₃ is

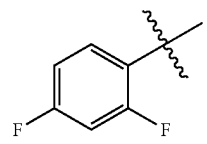 [SMILES: *c1ccc(F)cc1F]

Another embodiment of the present invention is a polyanhydride of the formula:

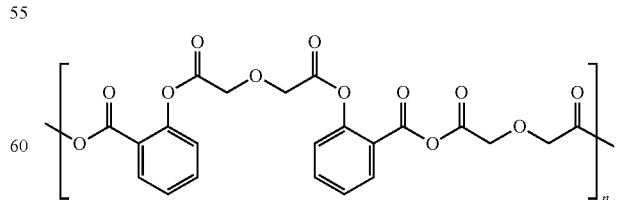

wherein n is a positive integer greater than 1.

Another embodiment of the present invention is a polyanhydride of the formula:

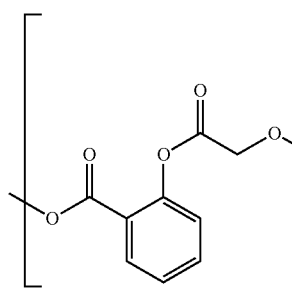

wherein n is a positive integer greater than 1.

Another embodiment of the present invention comprises administration of a composition comprising a therapeutically effective amount of a compound of the invention and a pharmaceutically acceptable vehicle to a mammal in need thereof.

A composition of the compound of formula (I) may usually be expected to elute the active agent faster than a polymer of formula (II).

When n of the polyanhydrides comprising a repeating unit is equal to an integer from 2 to 10, said polyanhydride is properly defined as an oligomer. In the case of the polyanhydride of formula (II) wherein p is 0, n is preferably 3 and/or 4. When n of the polyanhydride comprising a repeating unit having the structure of formula (II) is equal to an integer of 11 or higher, said polyanhydride is properly defined as a polymer. The molecular weight or the value of n is dependent on the desired properties of the polymer, for example, glass transition temperature, elasticity, tackiness, rate of hydration, rate of elution, etc. Preferably, n is an integer less than about 101, more preferably n is an integer less than about 21 and most preferably n is an integer less than about 11.

The compounds of the present invention contain an active agent, preferably a therapeutic agent, substituted with at least one hydroxyl group and optionally substituted with at least one carboxylic acid group prior to formation of the compound. Examples of such agents with these functional groups within their structure can be found in almost all therapeutic classes including, but not limited to, analgesics, anesthetics, anti-acne agents, antibiotics, synthetic antibacterial agents, anti-cancer agents, anticholinergics, anticoagulants, antidyskinetics, antifibrotics, anti-fungal agents, antiglaucoma agents, anti-infectives, steroidal and non-steroidal anti-inflammatory agents, anti-neoplastics, anti-osteoporotics, anti-pagetics, anti-Parkinson's agents, anti-psoratics, anti-pyretics, antiseptics/disinfectants, anti-thrombotics, bone resporption inhibitors, calcium regulators, keratolytics, sclerosing agents and ultraviolet screening agents. For preparing the compositions of the present invention, the use of therapeutic agents that fall within the classes of non-steroidal anti-inflammatory agents (NSAIDs), anti-infectives and anti-cancer agents are preferred.

Examples of therapeutic agents containing at least one hydroxyl group include anti-bacterials such as 4-sulfanilamidosalicylic acid, amoxicillin, apalcillin, apicycline, aspoxicillin, biapenem, cefadroxil, cefamandole, cefatrizine, cefbuperazone, cefdinir, cefonicid, cefoperazone, cefpiramide, cefprozil, flomoxef, imipenem, lucensomycin, lymecycline, meropenem, moxalactam, nadifloxacin, panipenem, ritipenem, salazosulfadimidine and sulfaloxic acid. Examples of anti-neoplastic therapeutic agents include carzinophillin A, denopterin, mycophenolic acid, streptonigrin, doxorubicin, paclitaxel, and gemcitabine. Examples of immunosupressants include mycophenolic acid. Examples of NSAIDs include diflunisal, fendosal, gentisic acid, mesalamine, salicylic acid, salsalate and sulfasalazine. The use of NSAIDs is particularly preferred, with salicylates such as salicylic acid, diflunisal, and salsalate being more preferred. Most preferred are salicylic acid and diflunisal.

Salicylates are anti-inflammatory, analgesic, anti-pyretic (fever reducing) and antiseptic compounds having antimicrobial activity. In particular, the salicylate salicylic acid is useful for the topical treatment and/or control of psoriasis, acne, microbially-derived malodor, dandruff, fungus, acne and wart removal. Salicylic acid is also known to be useful in limiting and in reducing scar formation and as a keratolytic agent. Salicylic acid is also used in cosmetic and personal skin care products and works as an exfoliant to reduce skin wrinkles and improve overall skin appearance of the face, body and scalp.

Other active agents useful in the invention are antioxidants, antiseptic agents and antibacterial agents.

The compositions of the invention are also useful for administering a combination of active agents, preferably therapeutic agents, to a mammalian host. Such a combination therapy can be carried out in the following ways: 1) a second active, preferably therapeutic, agent can be dispersed within the matrix of a composition of the present invention, and can be released upon degradation of the composition; 2) a second active, preferably therapeutic, agent can be appended to a composition of the present invention (e.g., as a sidechain on the polymer) with bonds that hydrolyze to release the second active, preferably therapeutic, agent under physiological conditions; 3) the compositions of the present invention can incorporate two or more different active, preferably therapeutic, agents into their structure (e.g., a polymer comprising one or more units of Formula (I) or a compound of formula (I), (II) or (III) in which D is different); or 4) two compositions of the present invention, each with a different active, preferably therapeutic, agent can be administered together (or within a short period of time). The invention also provides a pharmaceutical composition comprising a composition of the present invention, another active, preferably therapeutic, agent and a pharmaceutically acceptable vehicle.

As they degrade, the compositions of the present invention where the active, preferably therapeutic, agent is an NSAID do not cause the foreign body response and/or inflammatory response that is associated with other biodegradable polymers such as polylactides/glycolides (PLGAs) and polylactides (PLAs). Consequently, when the compositions of the present invention are used as a matrix to deliver a second therapeutic agent, the NSAIDs are preferred with salicylic acid and diflunisal being particularly preferred.

The conjugates, oligomers and polymers of the present invention may be analogously prepared as exemplified in the general synthetic schemes for diglycolate and triglycolate monomers and polymers below. Further synthesis information is provided in U.S. Patent Application 2005/0048121 (East et al.).

Scheme 1: Preparation of Diglycolate Monomers and Polymers

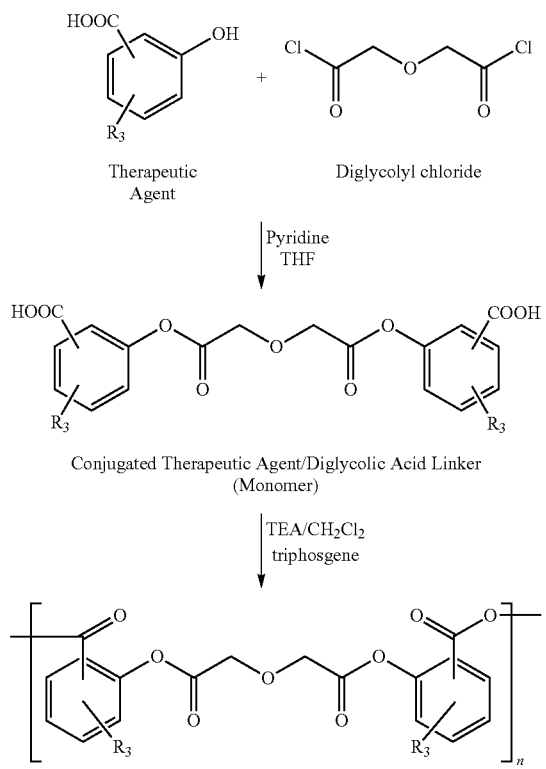

$R_3$ is selected from the group consisting of —H, —CF$_3$, —F, —Cl, —Br, —I, —OH, —NH$_2$, —NO$_2$, —CN, C$_1$ to C$_{12}$ straight-chain or branched alkyl, C$_1$ to C$_{12}$ alkoxy, C$_3$ to C$_{12}$ cycloalkyl, C$_3$ to C$_{12}$ cycloalkoxy, C$_1$ to C$_{12}$ alkanoyl, C$_1$ to C$_{12}$ alkanoyloxy, C$_1$ to C$_{12}$ alkoxy carbonyl, C$_1$ to C$_{12}$ alkylthio, azido, oxo, carboxy, aryl, aryloxy, heteroaryl, heteroaryloxy, and the following structures:

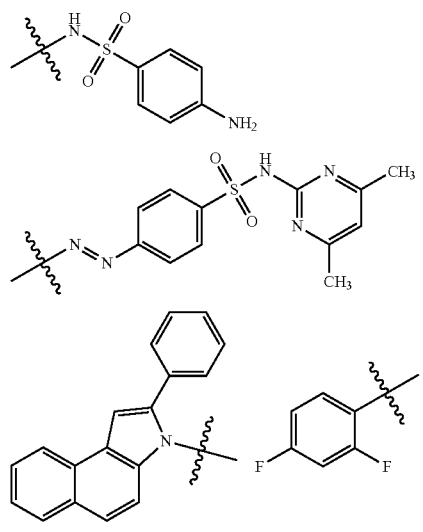

Scheme 2: Preparation of Triglycolic Diacid Monomers and Polymers

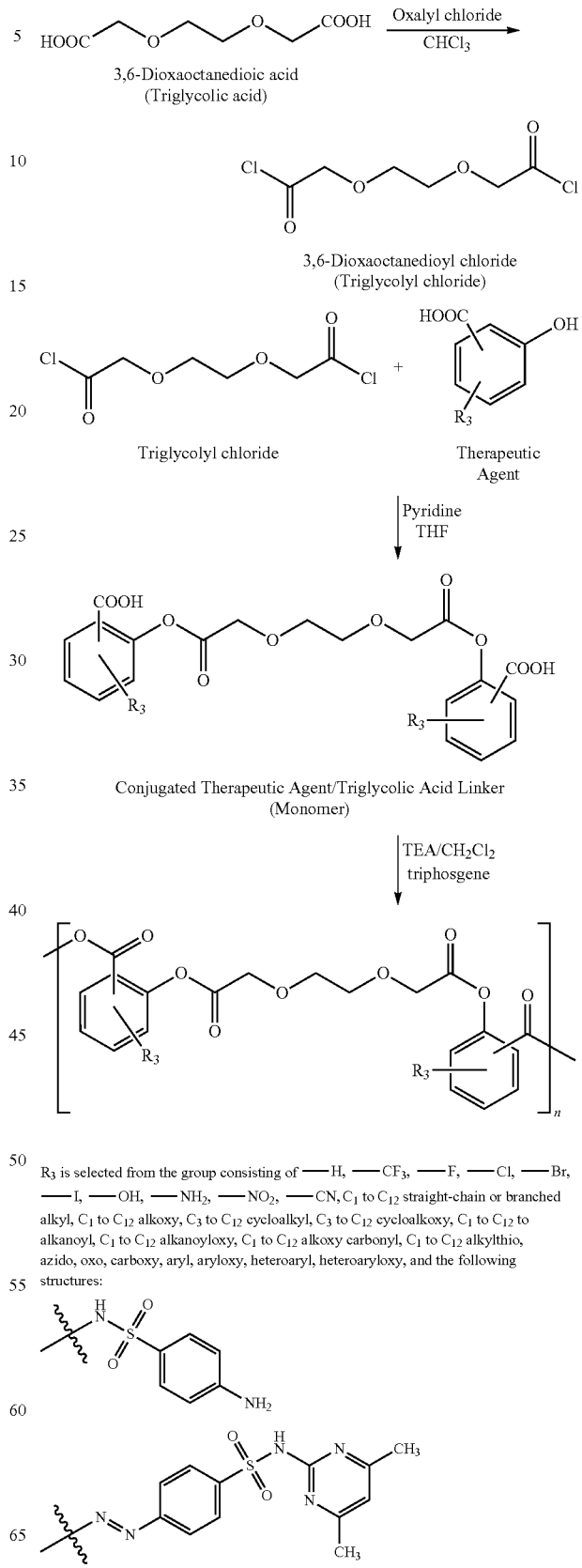

$R_3$ is selected from the group consisting of —H, —CF$_3$, —F, —Cl, —Br, —I, —OH, —NH$_2$, —NO$_2$, —CN, C$_1$ to C$_{12}$ straight-chain or branched alkyl, C$_1$ to C$_{12}$ alkoxy, C$_3$ to C$_{12}$ cycloalkyl, C$_3$ to C$_{12}$ cycloalkoxy, C$_1$ to C$_{12}$ alkanoyl, C$_1$ to C$_{12}$ alkanoyloxy, C$_1$ to C$_{12}$ alkoxy carbonyl, C$_1$ to C$_{12}$ alkylthio, azido, oxo, carboxy, aryl, aryloxy, heteroaryl, heteroaryloxy, and the following structures:

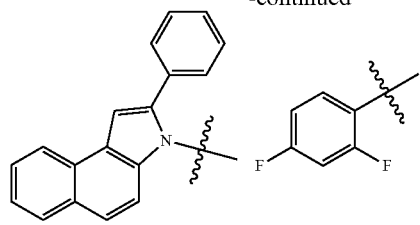

Scheme 3: Preparation of Salicylic Acid-Diglycolic Acid Linker-Salicylic Acid-Diglycolic Acid Linker Polymer

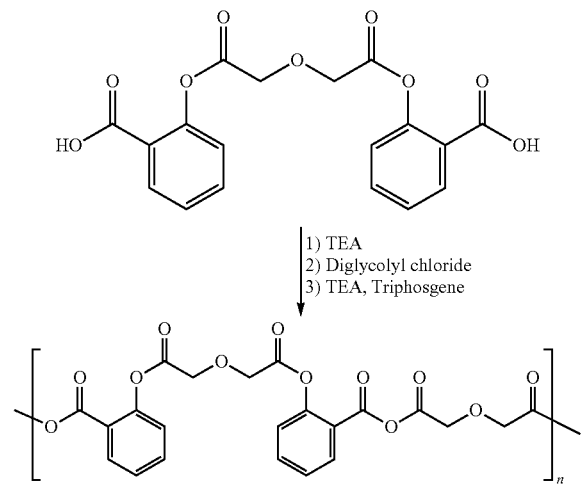

Scheme 4: Preparation of Salicylic Acid-Polyglycolic Diacid Linker-Salicylic Acid-Polyglycolic Diacid Linker Polymer

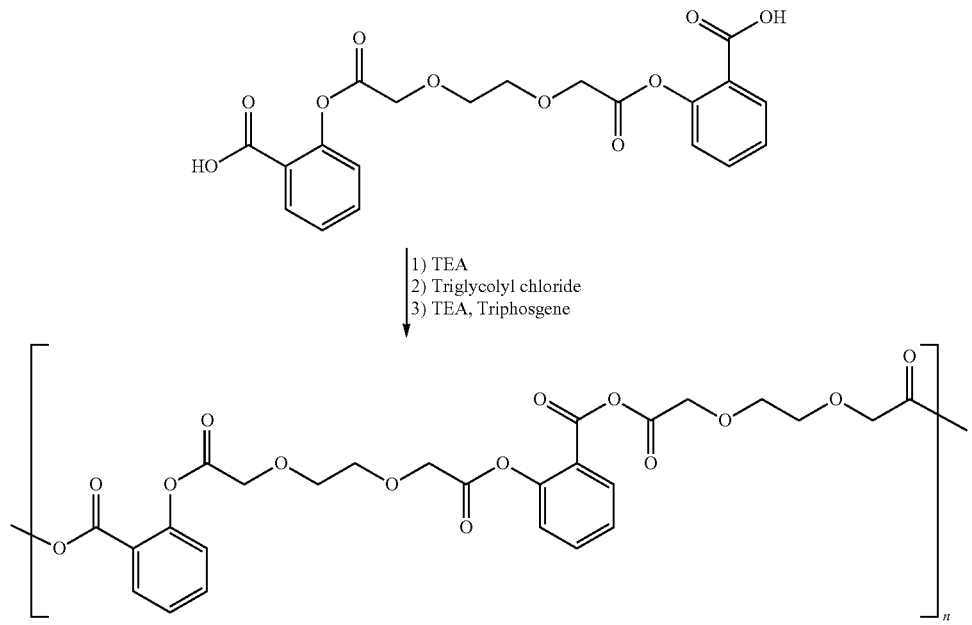

pharmaceutical, personal care, topical or coating compositions. Examples of topical use include personal care products, cosmetics and wound care products. For some uses, the compositions can conveniently be formulated as micronized particles or as nanoparticles.

Local administration of a pharmaceutical composition of a compound of the invention can occur in a wide variety of forms adapted to a chosen route of administration to a mammal, such as a human patient, e.g., rectally, parenterally, intravenously, intramuscularly, intraperitoneally, intraspinally (intrathecally), intracranially, topically, ocularly, and subcutaneously.

Therapeutic compositions of the present invention may be administered in combination with a pharmaceutically acceptable vehicle such as an inert diluent or an assimilable edible carrier. Such compositions and preparations preferably contain at least 0.1% of the inventive compound by weight. The percentage of the inventive compounds in preparations may be varied and may be between about 2% to about 80% of the weight, preferably about 2% to about 60%, of a given unit dosage form. The amount of therapeutic agent in such compositions is such that an effective dosage level will be obtained.

For topical use of a salicylic acid composition, generally the amount of the therapeutic agent released will range from about 0.5 to about 50 weight percent. For acne, (antimicrobial), anti-dandruff, psoriasis and anti-seborrhea, generally the amount of the salicylic acid released is about 0.5 to 2 percent and for wart removal, corn and callus removal generally about 12 to 40 percent when formulated in a plaster, 5 to 17 percent when formulated as a colloidion vehicle and about 15 percent when formulated as a karaya gum or glycol plaster.

Useful dosages of the inventive compounds can be determined by comparing their in vitro activity, and in vivo activity of the therapeutic agent in animal models. Methods for the extrapolation of effective dosages in mice, and other animals, to humans are known to the art; for example, see The compositions of the present invention are particularly suited for localized uses, for example, topical application, as a medical device or a coating and they can be formulated as U.S. Pat. No. 4,938,949. Additionally, useful dosages can be determined by measuring the rate of hydrolysis for a given composition under various physiological conditions. The amount required for use in treatment will vary not only with the particular composition selected but also with the route of administration, the nature of the condition being treated and the age and condition of the mammalian host and will be ultimately at the discretion of the attendant physician or clinician.

For localized administration, the present compositions can be applied in pure form. For example, the compounds may be applied as particles adhered to a bandage, gauze pad or other material, or may be formed into particles that are used in foot powders. However, it will generally be desirable to administer them as compositions, in combination with an acceptable vehicle for ease of application. For therapeutic use, the vehicle should be a dermatologically or pharmaceutically acceptable carrier, which may be a solid or a liquid. Useful solid carriers include finely divided solids such as talc, clay, microcrystalline cellulose, silica, alumina and the like. Useful liquid carriers include glycols or glycol blends, in which the present compounds can be dissolved or dispersed at effective levels, optionally with the aid of non-toxic surfactants. Adjuvants such as fragrances and additional anti-microbial agents can be added to optimize the properties for a given use. The resultant liquid compositions can be applied from absorbent pads, used to impregnate bandages and other dressings, or sprayed onto the target area using pump-type or aerosol sprayers or applied as an ointment, cream or lotion or coated onto wound care products such as dressings, sutures, meshes, etc. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the mammalian host. Examples of useful dermatological compositions which can be used to deliver the compositions of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

In another embodiment, the compositions of the present invention will be incorporated into personal care products, such as without limitation cleansing products, conditioning products, antiperspirants, shampoos, deodorants, lotions, creams and cosmetic items. Personal care products, particularly cleansing, conditioning and exfoliation products, have traditionally been marketed in a variety of forms such as bar soaps, shampoos, creams, lotions, powders and gels. Typically, these products have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and should not leave the skin or hair with a heavy buildup or overly dry when used frequently. The therapeutic agents in the conjugates, oligomers and polymers of the invention are released after administration of the personal care product and thereby provide the personal care product with the therapeutic advantage of the therapeutic agent. For example, by incorporating a compound of the invention containing as a therapeutic agent salicylic acid into a product, sustained delivery of salicylic acid to the skin surface may be obtained, which causes less skin irritation and which may reduce microbial derived malodor, dandruff, acne, skin wrinkles and/or improve overall skin appearance.

Because the compositions of the invention contain an active, preferably therapeutic, agent, the cleansing or conditioning methods also provide therapeutic treatment of the skin or hair according to the therapeutic indications associated with the particular agent that is incorporated into the conjugates, oligomers and polymers of the invention. Another embodiment of the present invention is a method for treating conditions of the hair, skin or scalp of a mammal comprising administering compositions of the inventive compounds to a mammal.

A personal care product for topical administration such as a cleansing and/or conditioning product for the hair and/or skin preferably contains one or more surfactants. Any suitable surfactant may be used. The surfactants of the cleansing component are preferably lathering surfactants. As used herein, "lathering surfactant" means a surfactant, which when combined with water and mechanically agitated generates a foam or lather. Such surfactants are preferred since increased lather is important to consumers as an indication of cleansing effectiveness. A wide variety of lathering surfactants are useful herein and include those selected from the group consisting of anionic lathering surfactants, nonionic lathering surfactants, cationic lathering surfactants, amphoteric lathering surfactants, and mixtures thereof.

Nonlimiting examples of surfactants useful in the compositions of the present invention are disclosed in McCutcheon's, Detergents and Emulsifiers, North American edition (1986), published by Allured Publishing Corporation; McCutcheon's, Functional Materials, North American Edition (1992); and U.S. Pat. No. 3,929,678, to Laughlin et al., issued Dec. 30, 1975.

Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and combinations thereof. Examples of alkyl ether sulfates which may be used include ammonium, sodium, magnesium, or TEA laureth-3 sulfate. Suitable alkyl sulfosuccinates include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid. Suitable alkyl ether carboxylates include sodium laureth carboxylate. Combinations of anionic surfactants can be used effectively in the present invention.

Other anionic materials include the carboxylates, nonlimiting examples of which include sodium lauroyl carboxylate, sodium cocoyl carboxylate, and ammonium lauroyl carboxylate. Anionic flourosurfactants can also be used. Other anionic materials include natural soaps derived from the saponification of vegetable and/or animal fats & oils such as sodium laurate, sodium myristate, palmitate, stearate, tallowate, cocoate. Any counter cation, M, can be used on the anionic surfactant. Preferably, the counter cation is selected from the group consisting of sodium, potassium, ammonium, monoethanolamine, diethanolamine, and triethanolamine. More preferably, the counter cation is ammonium.

Nonionic lathering surfactants useful herein include those selected from the group consisting of alkyl glucosides, alkyl polyglucosides, polyhydroxy fatty acid amides, alkoxylated fatty acid esters, sucrose esters, amine oxides, and mixtures thereof. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Suitable cationic lathering surfactants include, but are not limited to, fatty amines, di-fatty quaternary amines, tri-fatty quaternary amines, imidazolinium quaternary amines, and combinations thereof. Suitable fatty amines include monalkyl quaternary amines such as cetyltrimethylammonium bromide. A suitable quaternary amine is dialklamidoethyl hydroxyethylmonium methosulfate.

The term "amphoteric lathering surfactant," as used herein, is also intended to encompass zwitterionic surfactants, which are well known to formulators skilled in the art as a subset of amphoteric surfactants. A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

The compositions of the present invention may contain a variety of other components such as are conventionally used in a given product type provided that they do not unacceptably alter the benefits of the invention. These optional components should be suitable for application to human skin and hair, that is, when incorporated into the article they are suitable for use in contact with human skin without undue toxicity, incompatibility, instability, allergic response, and the like, within the scope of sound medical or formulator's judgment. The CTFA Cosmetic Ingredient Handbook, Second Edition (1992) describes a wide variety of non-limiting cosmetic and pharmaceutical ingredients commonly used in the skin care industry, which are suitable for use in the articles of the present invention. Examples of these ingredient classes include: enzymes, abrasives, skin exfoliating agents, absorbents, aesthetic components such as fragrances, pigments, colorings/colorants, essential oils, astringents, etc. (e.g., clove oil, menthol, camphor, eucalyptus oil, eugenol, methyl lactate, witch hazel distillate), anti-acne agents (e.g., resorcinol, sulfur, salicylic acid, erythromycin, zinc, etc.), anti-caking agents, antifoaming agents, additional antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, including agents for preventing, retarding, arresting, and/or reversing skin wrinkles (e.g., alpha-hydroxy acids such as lactic acid and glycolic acid and beta-hydroxy acids such as salicylic acid), thickeners, hydrocolloids, particular zeolites, and vitamins and derivatives thereof (e.g. tocopherol, tocopherol acetate, beta carotene, retinoic acid, retinol, retinoids, retinyl palmitate, niacin, niacinamide, and the like).

Compositions of the compounds of the invention may be used to form or coat shaped articles, including medical, dental and veterinary devices, such as vascular grafts and stents, bone plates, sutures, wound closing staples, surgical meshes, dental implants (e.g., dental, oro-maxillary, and alveolar), implantable sensors, implantable drug delivery devices, stents for tissue regeneration, catheters and other articles suitable for implantation or insertion into a patient. Examples of coatings for shaped articles are disclosed in U.S. Pat. No. 6,486,214; Australian Patent No. 750,424 B to Uhrich, U.S. App. Pub. No. 20050131199 A1 and U.S. App. Pub. No. 20050048121 A1.

Suitable devices that may be formed from or coated with compositions of the compounds of the invention also include stents, e.g., coronary vascular stents, peripheral vascular stents, urethral stents, biliary stents, stents used for supporting the lumen of other anatomical tubes, and stents used for other medical treatments; catheters, e.g., surgical catheters and urinary catheters; grafts; and orthopedic implants including, e.g., hip, knee and shoulder implants, internal and external fixation devices and spinal cages; drain tubes, endotrachael tubes, intravenous tubes, tampon applicators, tampons, ventilator tubes, endoscopes, arthroscopes, needles, condoms, barrier devices, diagnostic devices (e.g., speculum), dental appliances, and surgical appliances; balloons, guidewires, wound grafts, meshes, joint prostheses, breast prostheses, fracture management devices, drug dosing devices, pacemakers, mechanical pumps, defibrillators, and filters.

Suitable devices also include commercial devices such as those known in the art, including without limitation technologies described in: Stuart, M., "Technology Strategies, Stent and Deliver," *Start-Up, Windhover's Review of Emerging Medical Ventures*, pp. 34-38, June 2000); van der Giessen, Willem J., et al. "Marked Inflammatory Sequelae to Implantation of Biodegradable and Nonbiodegradable Polymers in Porcine Coronary Arteries," *Circulation*, Vol. 94, No. 7, pp. 1690-1697 (Oct. 1, 1996); Gunn, J. et al., "Stent coatings and local drug delivery," *European Heart Journal*, 20, pp. 1693-1700 (1999).

Compositions of the inventive compounds may be used as an anti-microbial to coat surfaces to inhibit or control mold, bacteria and biofilm growth. The compositions may be used to coat surfaces made from various materials, such as wood, metal, plastic (including nylon and polypropylene), paper, and fabric. The compounds and compositions of the invention may also be used in or to coat food wrappings, such as with an anti-bacterial or antioxidant active agent. The compounds may contain as active agents a fungicide, viracidal agent, or a bacteriocidal agent. Such compounds would be useful in industrial applications to prevent contamination and spoilage of a product otherwise susceptible to fungal, viral or bacterial attack.

The compositions of the invention may be applied to a surface by any means understood to those skilled in the art, such as by aerosol spray. To inhibit or control mold, bacteria and biofilm growth, the inventive compounds can be incorporated into paints, stains, coatings and other surface treatments that can applied to the target surface by brush, roller, spray or any other means that can deliver an effective amount of said compositions. The effect of inhibiting or controlling mold, bacterial and biofilm growth in vinyl construction materials can also be achieved by incorporating the compositions of the invention into such materials, such as vinyl siding, rather than merely applying the compositions to the surface of the materials.

The practice of the present invention is demonstrated by the Examples below which are not intended to limit the scope of the invention.

EXAMPLES

The following abbreviations are employed throughout the examples: DCM (dichloromethane), DF (diflunisal), SA (salicylic acid), TEA (triethylamine), THF (tetrahydrofuran), TP (triphosgene) and HCl (hydrochloric acid). All solvents and reagents employed in the following examples were purchased and used as received. Proton nuclear magnetic resonance ($^1$H NMR) spectra were recorded on a Varian 300 MHz Mercury VX-300 spectrometer using an appropriate deuterated solvent. Chemical shifts (δ) are reported in parts per million (ppm) downfield from tetramethylsilane (TMS) and coupling constants (J values) are given in hertz (Hz). Molecular weights ($M_w$) and polydispersity indices (PDI) were determined on a electron light scattering detector (ELSD), miniDAWN, along with a refractive index (RI) detector attached to a single pump system. Astra software was used for data collection and processing. Molecular weights were calibrated relative to a narrow molecular weight polystyrene standard (Viscotek, Houston, Tex.). The HPLC impurity profile was performed on an Agilent Rapid Phase C18 column 4.6×70 mm column and a different gradients of mobile phase A (0.1% (v/v) TFA in water) and mobile phase B (acetonitrile). A Mettler Toledo pH meter was used to measure pH using a 3-point calibration (pH 4.00, 7.00 and 10.00 standard solutions).

Example 1: Preparation of Bis(2-carboxyphenyl)diglycolate

To a stirred solution of 40.80 g of salicylic acid (0.296 mol) and 24 mL of anhydrous pyridine in 300 mL of anhydrous THF was added 24.8 g of diglycolyl chloride (0.145 mol) dissolved in 50 mL of anhydrous THF in a slow, drop-wise fashion. A white precipitate was formed during the addition. The reaction mixture was stirred at ambient temperature for an additional 30 minutes. The reaction mixture was poured into 2 L of ice-water containing 25 mL of conc. HCl. After stirring for 15 minutes, the white solid was filtered, and washed with water until the washings were neutral to pH paper. The product was dried overnight in a vacuum oven at 40° C. After drying, the crude product was twice suspended in 300 mL of hexane/ethyl acetate (75:25 v/v), stirred for 30 minutes and filtered. The product was dried overnight in a vacuum oven at 40° C. Isolated yield was 51 g. $^1$H NMR (CDCl$_3$) δ: 8.05 (dd, 2H, J=1.8 and 7.5 Hz), 7.53 (m, 2H), 7.32 (m, 2H), 7.15 (dd, 2H, H=1.8, 7.5 Hz), 6.84 (bs, 2H, exchanged with D$_2$O), 4.63 (s, 4H). $^{13}$C NMR (DMSO-d$_6$) δ: 169.2, 166.2, 150.3, 134.7, 132.3, 127.2, 124.4, 68.4.

Example 2: Preparation of Bis(2-carboxyphenyl)-3,6-dioxaoctanedioate

Step 1:

To a suspension of 7.13 g of 3,6-dioxaoctanedioic acid (0.04 mol) in 100 mL of anhydrous chloroform was added 10.3 mL of oxalyl chloride (0.12 mol) and the mixture was refluxed for 4 hours to give a clear solution. The solution was cooled to room temperature and the volatile components were removed in vacuo followed by further drying of the oily residue in vacuo to give the product in quantitative yield, which was used in the next step without further purification.

Step 2:

To a solution of 11.33 g of salicylic acid (0.082 mol) and 7.0 mL of anhydrous pyridine in 100 mL of anhydrous THF was added the triglycolyl chloride from step 1 (0.04 mol) in 50 mL of THF in a slow drop-wise fashion. A white precipitate was formed during the addition. The reaction mixture was stirred at ambient temperature for another 30 minutes and the whole reaction mixture was poured into 1.5 L of ice-water containing 8 mL of concentrated HCl. After stirring for 5 minutes, the product was separated as a semi-solid. The product was extracted into 200 mL of ethyl acetate, washed with 50 mL of water and 50 mL of brine solution. The organic layer was dried over 10 g of anhydrous sodium sulfate and filtered. Solvent was removed and the product was dried in vacuo. The oily crude product solidified upon standing at room temperature. The solid was powdered into fine particles, twice suspended into 150 mL of hexane-ethyl acetate (75:25 v/v), stirred for 30 minutes at room temperature, and filtered. The product was dried overnight in a vacuum oven at 40° C. Isolated yield was 8 g. $^1$H NMR (CDCl$_3$) δ: 7.93 (dd, 2H, J=1.8 and 7.5 Hz), 7.64 (m, 2H), 7.40 (m, 2H), 7.22 (dd, 2H, J=1.0, 7.9 Hz), 4.42 (s, 4H), 3.74 (s, 4H). $^{13}$C NMR (DMSO-d$_6$) δ: 169.8, 166.2, 150.4, 134.7, 132.2, 127.1, 124.5, 68.5, 41.1.

Comparative Example 1: Preparation of Bis(2-carboxyphenyl)adipate

To a stirred solution of 55.25 g of salicylic acid (0.4 mol) and 200 mL of anhydrous pyridine in 400 mL of anhydrous THF was added 36.6 g of adipoyl chloride (0.2 mol) dissolved in 100 mL of anhydrous THF in a slow, drop-wise fashion. A white precipitate was formed during the addition. The reaction mixture was stirred at ambient temperature for an additional 30 minutes. The reaction mixture was poured into 3 L of ice-water containing 25 mL of concentrated HCl. After stirring for 30 minutes, the white solid was filtered and washed with water until the washings were neutral to pH. The product was dried overnight in a vacuum oven at 40° C. After drying, the crude product was suspended in 300 mL of methanol and the resulting slurry was stirred for 45 minutes at ambient temperature and filtered. The product was dried overnight at 40° C. in a vacuum oven. Isolated yield was 75 g. $^1$H NMR (DMSO-d$_6$) δ: 13.08 (br s, 2H), 7.91 (dd, 2H, J=8.2, 1.2 Hz), 7.62 (ddd, 2H, J=7.6, 7.6, 1.2 Hz), 7.36 (ddd, 2H, J=7.6, 7.6, 1.2 Hz), 7.18 (dd, 2H, 8.2, 1.2 Hz), 2.61 (m, 4H), 1.73 (m, 4H). $^{13}$C NMR (DMSO-d$_6$) δ: 172.2, 166.4, 150.8, 134.4, 132.0, 126.7, 124.5, 124.5, 33.9, 24.2.

Example 3: Preparation of Poly[1,6-bis(2-carboxyphenyl)diglycolate]

To a stirred solution of 6 g of 1,6-bis(2-carboxyphenyl) diglycolate (0.016 mol) in 60 mL of anhydrous DCM was added 5.4 mL of TEA (0.038 mol) at 0° C. A solution of 1.7 g of triphosgene in 20 mL of DCM was added to the solution in a slow drop-wise fashion. The reaction mixture was stirred for an additional 30 minutes and then transferred to a 250 mL separatory funnel. The solution was washed with 100 mL of 1N HCL, 100 mL of water and brine solution. The organic layer was dried over 10 g of anhydrous magnesium sulfate. The solution was filtered and the solvent was evaporated to a volume of about 30 mL. The polymer solution was added to 300 mL of anhydrous pentane with stirring. The precipitated polymer was isolated by filtration, and dried in a vacuum oven at 60° C. for 24 hours. Mw=13.6 K; PDI=6.0; $^1$H NMR (CDCl$_3$) δ: 8.10-7.99 (m, 2H), 7.71-7.59 (m, 2H), 7.44-7.30 (m, 2H), 7.25-7.16 (m, 2H), 4.54-4.50 (m, 4H).

Example 4: Preparation of Poly[1,6-bis(2-carboxyphenyl)diglycolate]

To a stirred solution of 7.41 g of 1,6-bis(2-carboxyphenyl) diglycolate (0.02 mol) in 60 mL of anhydrous DCM was added 5.6 mL of TEA (0.038 mol) at 0° C. A solution of 1.7 g of TP in 20 mL of anhydrous DCM was added to the solution in a slow drop-wise fashion. The reaction mixture was stirred for an additional 2 hours and then transferred to a 250 mL separatory funnel. The solution was washed with 100 mL of 1 N HCl and with 100 mL of water twice. A white precipitate formed during the washing was collected by filtration, washed with water, and dried at 50° C. (Example 4A). The organic layer was washed with brine, dried over anhydrous magnesium sulfate, filtered, and the solvent was removed in vacuo. The residue was dried at 50° C. in a vacuum oven (Example 4B). $^1$H NMR (Example 4A, CDCl$_3$) δ: 8.12 (dd, J=1.8 & 7.9 Hz), 8.06 (dd, J=1.8 & 7.9 Hz), 7.73 (t, J=6.2 Hz), 7.60 (t, J=6.9 Hz), 7.47 (t, J=7.2), 7.35 (m), 7.16 (d, J=8.3 hz), 4.65 (s), 4.53 (s). Mw=2.1 K; $^1$H NMR (Example 4B, CDCl$_3$) δ: 8.13-8.01 (m), 7.75-7.61 (m), 7.59-7.10 (m), 4.65-4.53 (m). Mw=1.6 K.

Comparative Example 2: Preparation of Poly[1,6-bis(2-carboxyphenyl)adipate]

A 250 mL 3-neck flask was charged with 1,6-bis(2-carboxyphenyl) adipate (15.46 g, 0.04 mol.) and 100 mL of anhydrous DCM A slow argon flow was maintained in the flask while the reaction mixture was cooled to 0±4° C. TEA (13.94 mL, 0.1 mol.) was added to the reaction flask with stirring. TP (3.96 g) was weighed into a separate flask, dissolved in 25 mL of anhydrous DCM, and was added to the cooled solution of the monomer in a slow drop-wise fashion. After the addition was complete, the reaction mixture was stirred for another 30 minutes and the polymer solution was transferred to a 250 mL separatory funnel. The polymer solution was washed with 1N HCL (100 mL), water (2×100 mL) and aqueous sodium chloride solution. The organic layer was dried over anhydrous magnesium sulfate (10.0 g). The solution was filtered into a 250 mL round-bottom flask and then the solvent was removed on a rotary evaporator to reduce the volume to about 80 mL. The polymer solution was added to anhydrous ether (800 mL) with stirring. The precipitated polymer was dried in a vacuum oven at 40° C. Yield was 11 g. Mw=11.3 K; PDI=1.30; $^1$H NMR (CDCl$_3$) δ: 8.07-8.02 (m, 2H), 7.66-7.60 (m, 2H), 7.36-7.31 (t, 2H, J=7.86 Hz), 7.16 (d, 2H, J=7.92), 2.58 (bs, 4H), 1.72 (bs, 4H).

Example 5: Preparation of 6-Bis[(2-carboxy-4(2',4'-difluorophenyl)phenyl]glycolate To a solution of 10.50 g of diflunisal (0.042 mol.) and 3.7 mL of anhydrous pyridine (0.045 mol.) in 100 mL of anhydrous THF was added 3.42 g of diglycolyl chloride (0.02 mol.) in 25 mL of anhydrous THF 1 in a slow drop-wise fashion. A white precipitate was formed during the addition. The reaction mixture was stirred at ambient temperature for an additional 30 minutes. The reaction mixture was poured into 1 L of ice-water containing 5 mL of conc. HCl. After stirring for 15 minutes, the white precipitate was filtered and washed with water until the washings were neutral to pH paper. The product was dried overnight in a vacuum oven at 40° C. After drying, the crude product was suspended in 100 mL of hexane/ethyl acetate (75:25, v/v) solvent mixture, stirred for 30 minutes, and filtered. The product was dried overnight in a vacuum oven at 40° C. Isolated yield was 11 g. $^1$H NMR (CDCl$_3$+DMSO-d$_6$): 7.96 (d, 2H, J=1.3 Hz), 7.48 (dd, 2H, J=6.5 and 1.8 Hz), 7.26-7.02 (m, 2H), 7.0 (d, 2H, J=8.2 Hz), 6.80-6.68 (m, 4H), 4.52 (bs, exchanged with D$_2$O), 4.45 (s, 4H)

Example 6: Preparation of 1,6-Bis[(2-carboxy-4(2',4'-difluorophenyl)phenyl)]-3,6-dioxaoctanedioate The composition was synthesized on a 0.40 mole scale following the same procedure used for Example 2. Yield after isolation and purification was 19 g. $^1$H NMR (CDCl$_3$+DMSO-d$_6$): 8.04 (d, 2H, J=1.8 Hz), 7.80 (dd, 2H, J=1.6, 6.5 Hz), 7.68-7.60 (m, 2H), 7.42-7.34 (m, 4H), 7.23-7.17 (m, 2H).

Example 7: Preparation of Poly{1,6-Bis[(2-carboxy-4(2',4'-difluorophenyl)phenyl]}glycolate To a cooled, stirred solution of 8.62 g of the diacid of Example 6 (0.15 mol.) in 75 mL of anhydrous DCM was added 5.0 mL of TEA. A solution of 1.7 g of TP in 20 mL of anhydrous DCM was added to the diacid solution in a slow drop-wise fashion. The reaction mixture was stirred for an additional 2 hours and then transferred to a 250 mL separatory funnel. The solution was washed with 50 mL of 1N HCl, 50 mL of water and dried over anhydrous sodium sulfate. The solution was filtered into a 250 mL round bottom flask and the solvent was removed to dryness. Isolated yield was 7.5 g. Mw=2.6 K; $^1$H NMR (CDCl$_3$): 8.21-8.13 (m), 7.82-7.75 (m), 7.48-7.16 (m), 7.02-6.86 (m), 4.74-4.51 (m).

Example 8: Preparation of the Salicylic Acid-Diglycolic Acid Linker-Salicylic Acid-Diglycolic Acid Linker Polymer of Scheme 3

A solution of diglycolyl chloride (3.42 g, 0.02 mol) in anhydrous DCM (50 mL) is added to a solution of DGA bisSA diacid (7.49 g, 0.02 mol, prepared in example 1) and TEA (6.13 mL, 0.044 mol) in anhydrous DCM (30 mL) slowly at 0° C. After the completion of the addition, the reaction solution is stirred for 1 h and diluted with DCM (100 mL). The solution is washed with 1N HCl (2×150 mL) and distilled water (100 mL), and dried over anhydrous MgSO$_4$. The solution is concentrated in vacuo to dryness to give the polymer. The polymer is dissolved in anhydrous DCM (100 mL) and TEA (4 equivalents of $M_n$ of pre-polymer) is added at 0° C. A solution of triphosgene in anhydrous DCM is added very slowly to the polymer solution at 0° C. The addition of triphosgene is continued until the target $M_w$ is reached by GPC (as monitored by running an aliquot through GPC). After the reaction is completed, the mixture is diluted with DCM, washed with 1N HCl (2×150 mL) and distilled water (150 mL), and dried over anhydrous MgSO$_4$. The solution is concentrated in vacuo till a thick oil is obtained and dropped into anhydrous diethyl ether (DCM solution-ether=1:5, v/v) in a Teflon cylinder with stirring to precipitate the final polymer. The solid is washed further with diethyl ether and dried in the vacuum oven overnight at 40° C. to give the product.

Example 9: Preparation of the Salicylic Acid-Polyglycolic Diacid Linker-Salicylic Acid-Polyglycolic Diacid Linker Polymer of Scheme 4

A solution of triglycolyl chloride (4.30 g, 0.02 mol, prepared in Example 2, step 1) in anhydrous DCM (50 mL) is added to a solution of TGA bisSA diacid (8.37 g, 0.02 mol, prepared in example 2) and TEA (6.13 mL, 0.044 mol) in anhydrous DCM (30 mL) slowly at 0° C. After the completion of the addition, the reaction solution is stirred for 1 h and diluted with DCM (100 mL). The solution is washed with 1N HCl (2×150 mL) and distilled water (100 mL), and dried over anhydrous $MgSO_4$. The solution is concentrated in vacuo to dryness to give the polymer. The polymer is dissolved in anhydrous DCM (100 mL) and TEA (4 equivalents of $M_n$ of pre-polymer) is added at 0° C. A solution of triphosgene in anhydrous DCM is added very slowly to the polymer solution at 0° C. The addition of triphosgene is continued until the target $M_w$ is reached by GPC (monitored by running an aliquot through GPC). After the reaction is completed, the mixture is diluted with DCM, washed with 1N HCl (2×150 mL) and distilled water (150 mL), and dried over anhydrous $MgSO_4$. The solution is concentrated in vacuo till a thick oil is obtained and dropped into anhydrous diethyl ether (DCM solution-ether=1:5, v/v) in a Teflon cylinder with stirring to precipitate the final polymer. The solid is washed further with diethyl ether and dried in the vacuum oven overnight at 40° C. to give the product.

Example 10: Particle Size Determination

Light scattering techniques were employed to assess the particle size distributions of samples of the compositions of Examples 1 and 2 and Comparative Example 1. Results are shown in Table 1 below:

TABLE 1

Particle Size Distribution

| Sample | Volume Mean Particle Diameter (μm) | Average[1] % of particles below 10 μm | Average % of particles below 100 μm | Average % of particles below 200 μm | Comments |
|---|---|---|---|---|---|
| Example 1 | 45.64 | 11.87 | 91.69 | 99.58 | |
| Example 2 | 48.82 | 37.54 | 80.89 | 99.39 | Bimodal size distribution |
| Comparative Example 1 | 28.85 | 32.1 | 96.03 | 99.99 | |

[1]Values reflect an average of 3 samples assessed for particle size

Optimum particle size range for skin deposition is believed to be between 1 and 40 microns. Current samples were on average larger than desired, however, samples did contain a substantial percent of particles that fell within the target range.

Example 11: Salicylic Acid Release into Artificial Sweat

Samples of Example 1 and 2 and Comparative Example 1 were placed in artificial sweat or artificial sweat plus proteins and incubated at 35° C. for 3 to 5 minutes, 1, 2, 4, 6 and 24 hours, rapidly filtered (0.22 μm filter) and analyzed for salicylic acid by HPLC.

TABLE 2

Salicylic Acid Release (Weight Percent of Maximum Release)

| Time (hrs) | Ex. 1 | Ex. 2 | Comp. Ex. 1 |
|---|---|---|---|
| 0.05 | 20.035 | 35.25 | 1.46 |
| 1 | 45.525 | 47.44 | 4.93 |
| 2 | 54.910 | 44.85 | 6.03 |
| 4 | 59.795 | 46.07 | 6.81 |
| 6 | 54.890 | 51.20 | 10.06 |
| 24 | 64.520 | 58.23 | 26.42 |

Examples 1 and 2 showed rapid initial salicylic acid release rates while Comparative Example 1 exhibited a more moderate salicylic acid release rate. From these results, Examples 1 and 2 best met the target of 50% salicylic acid release within 24 hours. See FIG. 1 for a graphical representation of the results in Table 2.

Example 12: Antibacterial Activity

Samples of Examples 1 and 2 and Comparative Example 1 were evaluated in two different bacterial growth assays. The first test was a standard Minimum Inhibitory Concentration (MIC) assessment involving serial dilution of test compound particle suspensions in water. In this test, the samples were evaluated at 24 hours against human derived *Staphylococcus epidermidis* and *Corynebacter* sp. form organisms. The second test utilized a Biosys® system to assess the effect of the samples added as a dry powder directly to a nutrient broth containing either human derived *Staph epidermidis* or a mixed *Coryne/Staph* milieu. In the case of the Biosys test, the bacteria laced nutrient broth alone was used as the negative control.

Table 3 shows the MIC values obtained for the samples against the target organisms; Table 4 shows the Biosys values obtained for the samples against *Staphylococcus epidermidis*; and Table 5 shows the Biosys values obtained for the samples against a mixed *Corynebacter/Staph* system.

TABLE 3

MIC Values

| Test System | MIC versus *Staph epidermidis* mg/ml | MIC versus *Coryne* form mg/ml |
|---|---|---|
| Example 1 | ~0.2-1 | ~0.2 |
| Example 2 | ~2.5 | — |
| Comparative Example 1 | >1.67 | >1.67 |

Example 1 had the strongest antibacterial activity of the samples tested. Example 2 exhibited modest antibacterial activity against *Staph. epi* while Comparative Example 1 exhibited little or no antibacterial activity at the concentrations evaluated.

TABLE 4

Biosys *Staph epidermidis* Values

| Test System | % Red[1] 50 mg/ml | % Red 5 mg/ml | % Red 2.5 mg/ml | % Red 0.5 mg/ml | % Red 0.25 mg/ml |
|---|---|---|---|---|---|
| Example 1 | 100 | 100 | 100 | 95 | 10 |
| Example 2 | 100 | 100 | 50 | 0 | 0 |
| Comparative Example 1 | 100 | 100 | 63 | 57 | 0 |

[1]% average reduction in bacterial growth rates at 24 hours.

Example 1 provided the strongest antibacterial activity of the samples.

TABLE 5

Biosys Mixed *Coryne/Staph* Values

| Test System | % Red[1] 50 mg/ml | % Red 5 mg/ml | % Red 2.5 mg/ml | % Red 0.5 mg/ml | % Red 0.25 mg/ml |
|---|---|---|---|---|---|
| Example 1 | 100 | 100 | 100 | 29 | 66 |
| Example 2 | 100 | 100 | 100 | 0 | 5 |
| Comparative Example 1 | 100 | 100 | 6 | 5 | 0 |

[1]% average reduction in bacterial growth rates at 24 hours.

Example 1 provided the strongest antibacterial activity of the samples. The degree of activity of Example 1 is provides an indication of usefulness in a personal care product.

Example 13

Examples 1, 3 and 4 (both A & B) and Comparative Examples 1 and 2 were evaluated for rate of release of salicylic acid. Samples were hydrolyzed at 32° C. using acetate buffer (pH 5.5) as relevant condition for typical skin pH. The materials were placed in 50 mL centrifuge tubes for elution using conventional elution protocols, shaking the tubes in a thermostatic environment. Aliquots were taken from the tubes at periodic intervals and immediately placed in a vial and analyzed by HPLC as soon as they were removed from the hydrolysis vessel.

Figure 2:
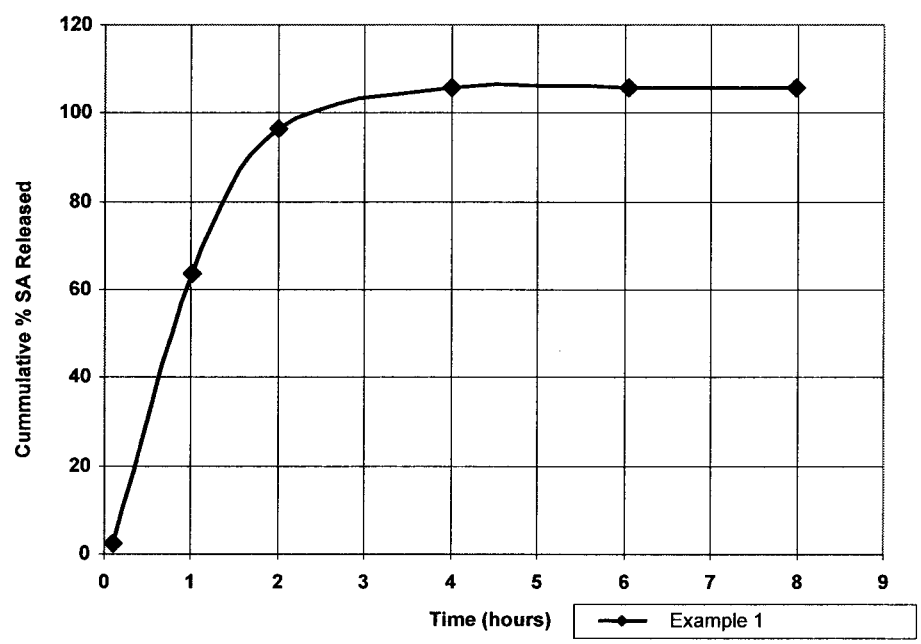
FIG. 2 illustrates cumulative percent release of salicylic acid over time from Example 1. Samples were hydrolyzed at 32° C. using acetate buffer (pH 5.5) and aliquots were taken at periodic intervals and analyzed by HPLC.
Figure 3:
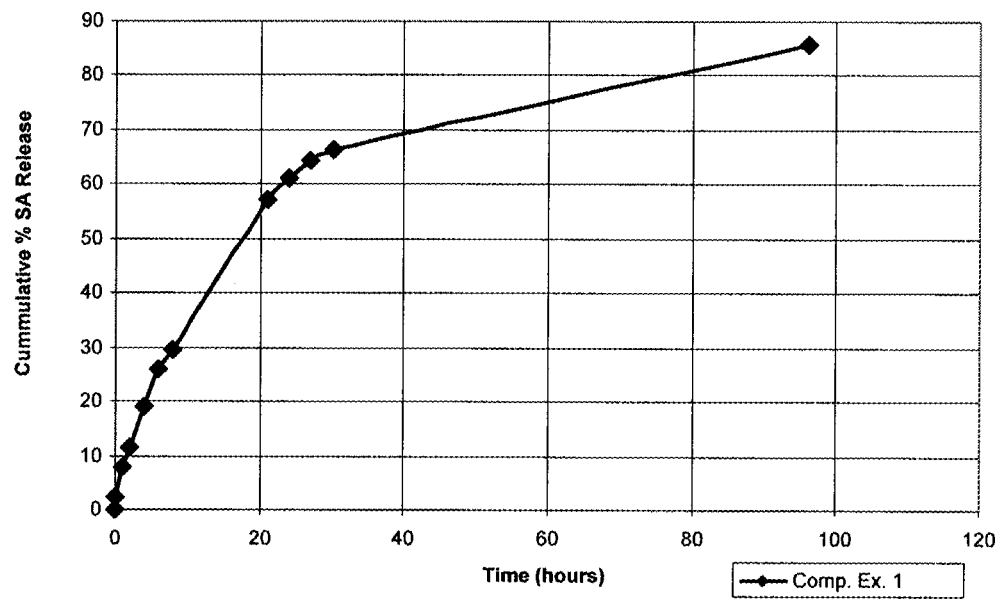
FIG. 3 illustrates cumulative percent release of salicylic acid over time from Comparative Example 1. Samples were hydrolyzed at 32° C. using acetate buffer (pH 5.5) and aliquots were taken at periodic intervals and analyzed by HPLC.

Example 1 hydrolyzed more rapidly than Comparative Example 1. Comparative Example 1 achieves about 90% completion in four days, while Example 1 is complete in 2.5 hours. The results are illustrated in FIG. 2 (Example 1) and 3 (Comparative Example 1) and indicate an increase in rate of hydrolytic release of therapeutic agent in having the oxygen in the backbone of the linker, as well as α-alkoxy carboxylic acid ester groups as the moiety that connects the linker to the therapeutic agent.

Figure 4:
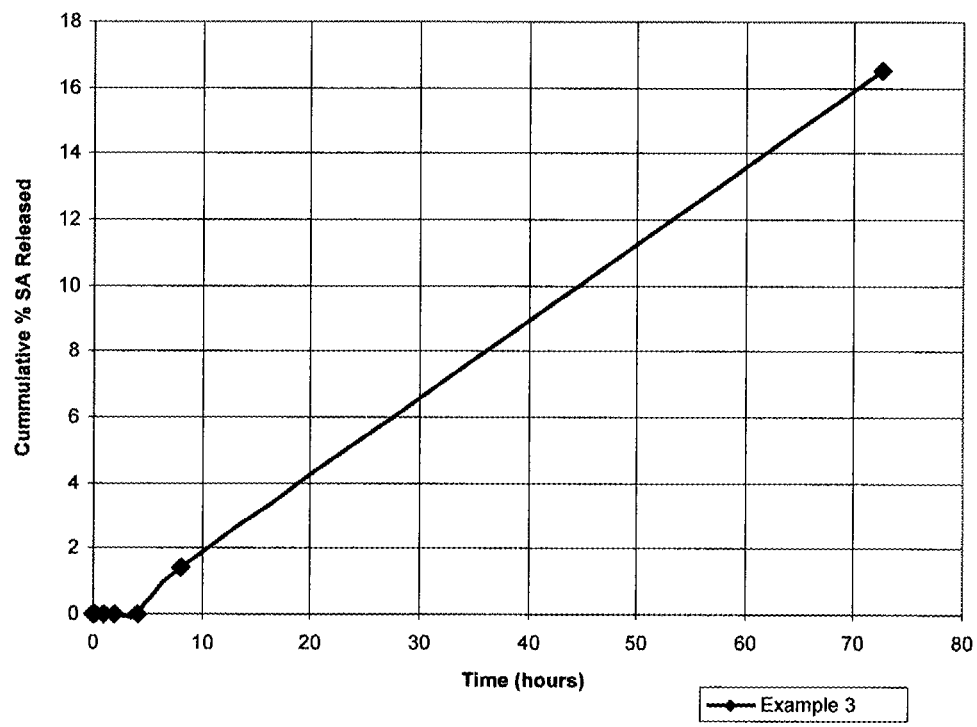
FIG. 4 illustrates cumulative percent release of salicylic acid over time from Example 3. Samples were hydrolyzed at 32° C. using acetate buffer (pH 5.5) and aliquots were taken at periodic intervals and analyzed by HPLC.

After three days, Example 3 had achieved only 17% hydrolysis, while Comparative Example 2 had achieved even less. The results for Example 3 are illustrated in FIG. 4.

Figure 5:
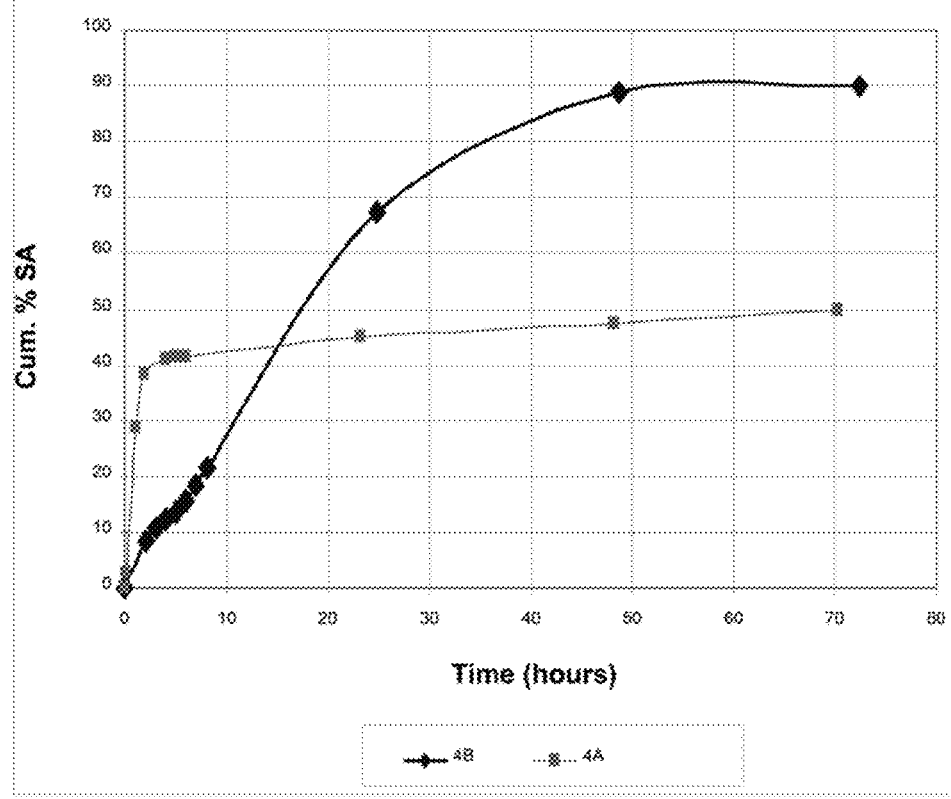
FIG. 5 illustrates the comparison of cumulative percent release of salicylic acid over time from Example 4A (square) and Example 4B (diamond). Samples were hydrolyzed at 32° C. using acetate buffer (pH 5.5) and aliquots were taken at periodic intervals and analyzed by HPLC.
Figure 6:
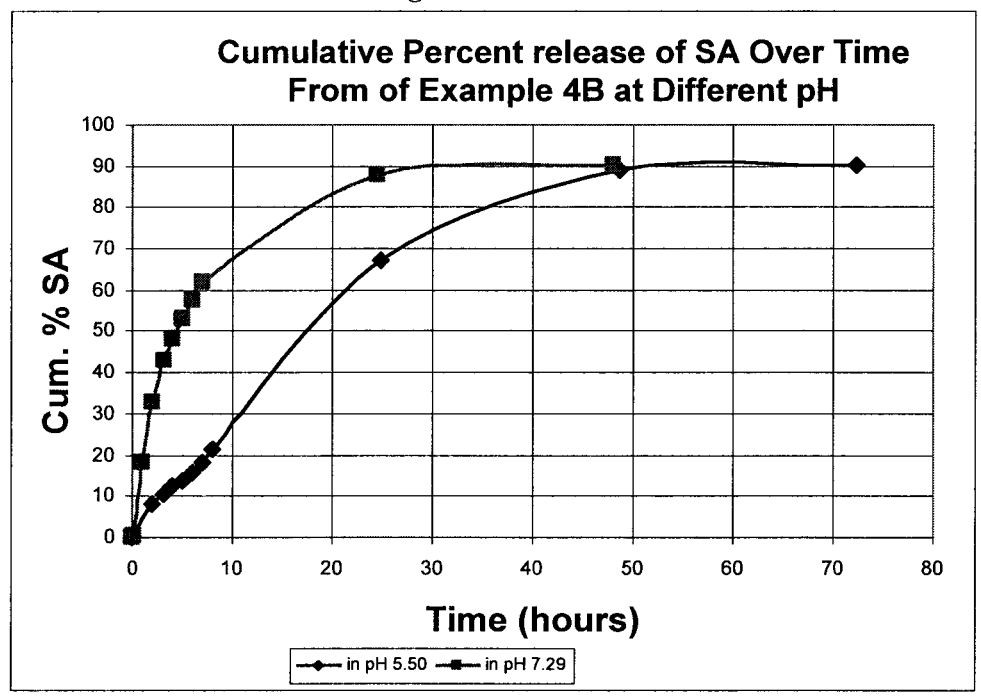
FIG. 6 illustrates cumulative percent release of salicylic acid over time from Example 4B at pH 5.50 (diamond) and pH 7.29 (square). Samples were hydrolyzed at 32° C. using either acetate buffer (pH 5.5) or PBS buffer (pH 7.29) and aliquots were taken at periodic intervals and analyzed by HPLC.

The material of Example 4A had a fast initial elution and then plateaued at 50% completion. The material of Example 4B had a $T_{1/2}$ of about 18 hours. This material was also hydrolyzed using PBS buffer (pH 7.29), which resulted in a faster breakdown and a $T_{1/2}$ of approximately 5.5 hours. The respective salicylic acid release rates of the Example 4A and Example 4B at pH 5.5 are compared in FIG. 5. The rates of Example 4B at pH of 5.5 and 7.29 are compared in FIG. 6.

Significantly slower hydrolysis of the polymers relative to monomers possibly suggests that it is the effect of higher hydrophobicity of the polymer resulting in a slower hydration rate. The polymers of Example 3 and Comparative Example 2, by being overall more nonpolar, have more hydrophobicity and less access to water for hydrolysis to proceed. The rate of hydrolysis appears to be also dependent on the effect of the carboxylic acids on the hydrophilicity and polarity relative to the size of the molecule. This effect may be reduced as the polymer grows in length.

These examples are meant to describe and not limit the invention, as modifications will be apparent to one skilled in the art. Also, all of the articles, patent publications and other references referred to herein are expressly incorporated by reference herein in their entireties.

What is claimed is:

1. A compound according to formula (I):

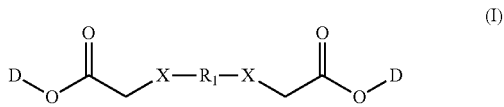

wherein each D is the same or different and is a therapeutic agent selected from 4-sulfanilamidosalicylic acid, amoxicillin, apalcillin, apicycline, aspoxicillin, biapenem, cefadroxil, cefamandole, cefatrizine, cefbuperazone, cefdinir, cefonicid, cefoperazone, cefpiramide, cefprozil, flomoxef, imipenem, lucensomycin, lymecycline, meropenem, moxalactam, nadifloxacin, panipenem, ritipenem, salazosulfadimidine, sulfaloxic acid, carzinophillin A, denopterin, mycophenolic acid, streptonigrin, doxorubicin, paclitaxel, gemcitabine, mycophenolic acid, diflunisal, fendosal, gentisic acid, mesalamine, salicylic acid, salsalate, and sulfasalazine, $R_1$ is selected from the group consisting of $[(CH_2)_xO]_y(CH_2)_w$—, —$(CH_2)_y$—, —$[CH=CH—O]_y(CH_2)_z$—, —$[(CH=CH—CH_2—O]_y(CH_2)_z$—, $[CH_2—CH=CH—O]_y(CH_2)_z$—, —$[(CH_2)_xO]_y(CH=CH)$—, wherein w is 1 or 2, x is 2 or 3, and y is equal to an integer from 1 to 10, from 1 to 4, or from 1 to 3, z is equal to 1 or 2, and the carbon atoms of $R_1$ may be optionally substituted with substituents selected from the group consisting of $C_1$ to $C_{12}$ alkyl, $C_1$ to $C_{12}$ alkoxy, $C_3$ to $C_{12}$ cycloalkyl, $C_3$ to $C_{12}$ cycloalkoxy, $C_1$ to $C_{12}$ alkanoyl, $C_1$ to $C_{12}$ alkanoyloxy, $C_1$ to $C_{12}$ alkoxy carbonyl, $C_1$ to $C_{12}$ alkylthio, azido, cyano, nitro, fluoro, chloro, bromo, iodo, hydroxy, oxo, carboxy, aryl, aryloxy, heteroaryl, and heteroaryloxy;

each X is the same or different and is selected from the group consisting of —O—, —$NR_2$—, —S—, —SO—, and —$SO_2$—, wherein $R_2$ is an alkyl group of 1 to 12 carbon atoms.

2. The compound of claim 1 having the formula:

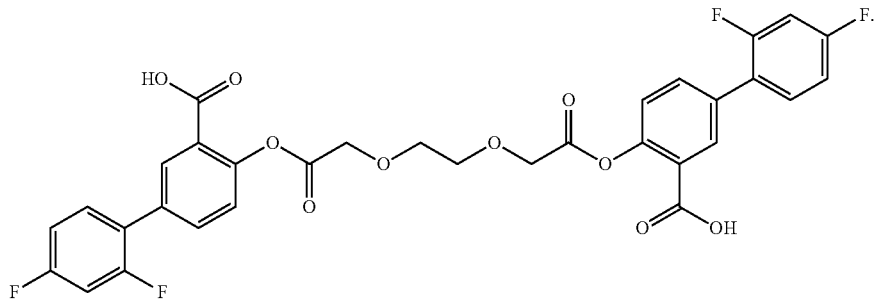 [SMILES: O=C(COCCOCC(=O)Oc1ccc(-c2ccc(F)cc2F)cc1C(=O)O)Oc1ccc(-c2ccc(F)cc2F)cc1C(=O)O]

3. A composition comprising the compound of claim 1 and a dermatologically or pharmaceutically acceptable carrier.

4. A topical composition comprising the compound:

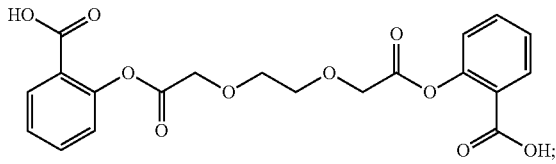 [SMILES: O=C(COCCOCC(=O)Oc1ccccc1C(=O)O)Oc1ccccc1C(=O)O]

and a dermatologically or pharmaceutically acceptable carrier.

5. The compound of claim 1, wherein each D is an anti-inflammatory agent, and the anti-inflammatory agents are non-steroidal anti-inflammatory agents selected from the group consisting of diflunisal, fendosal, gentisic acid, mesalamine, salicylic acid, salsalate and sulfasalazine.

6. The topical composition of claim 4 further comprising a second active agent selected from an anti-inflammatory agent, anti-infective agent, antibacterial agent, antiseptic agent, and antioxidant.

7. The topical composition of claim 4 wherein the composition is formulated as micronized particles or as nanoparticles.

8. The topical composition of claim 4 wherein the composition contains at least 0.1% of the inventive compound by weight.

9. The topical composition of claim 4 wherein the composition contains the compound between about 2% to about 80% of the weight.

10. The topical composition of claim 4 wherein the composition contains the compound between about 2% to about 60% of the weight.

11. The topical composition of claim 4 wherein the composition is in the form of a plaster, a colloidion vehicle, a karaya gum, or glycol plaster.

12. The topical composition of claim 4 wherein the composition is a liquid.

13. The topical composition of claim 4 wherein the composition is a solid.

14. The topical composition of claim 4 wherein the dermatologically or pharmaceutically acceptable carrier comprises talc, clay, microcrystalline cellulose, silica, or alumina.

15. The topical composition of claim 4 wherein the composition is a deodorant, antiperspirant, lotion, cream, shampoo, conditioning product, cleansing product, or exfoliation product.

16. The topical composition of claim 4 further comprising a surfactant, an exfoliating agent, an astringent, an anti-acne agent, a humectant, or a combination thereof.

* * * * *